(12) United States Patent
Greenhalgh et al.

(10) Patent No.: US 8,636,784 B2
(45) Date of Patent: Jan. 28, 2014

(54) EXPANDABLE ATTACHMENT DEVICE AND METHOD

(75) Inventors: E. Skott Greenhalgh, Lower Gwynedd, PA (US); John-Paul Romano, Chalfont, PA (US); Michael Paul Igoe, Seabrook, TX (US); Robert A. Kiefer, Quakertown, PA (US); Wade Kevin Trexler, Coopersburg, PA (US)

(73) Assignee: Stout Medical Group, LP, Perkasie, PA (US)

( * ) Notice: Subject to any disclaimer, the term of this patent is extended or adjusted under 35 U.S.C. 154(b) by 816 days.

(21) Appl. No.: 12/264,181

(22) Filed: Nov. 3, 2008

(65) Prior Publication Data

US 2009/0131992 A1 May 21, 2009

Related U.S. Application Data

(60) Provisional application No. 60/985,087, filed on Nov. 2, 2007.

(51) Int. Cl.
*A61B 17/86* (2006.01)

(52) U.S. Cl.
USPC .......................... 606/313; 606/327

(58) Field of Classification Search
USPC ............... 606/300–321; 623/17.11–17.16; 411/519; 433/167, 173–174, 177, 433/180–183
See application file for complete search history.

(56) References Cited

U.S. PATENT DOCUMENTS

| | | | |
|---|---|---|---|
| 1,438,648 A * | 12/1922 | Jacobs | 411/386 |
| 4,738,255 A | 4/1988 | Goble et al. | |
| 5,037,422 A | 8/1991 | Hayhurst et al. | |
| 5,046,513 A | 9/1991 | Gatturna et al. | |
| 5,065,490 A | 11/1991 | Wivagg et al. | |
| 5,207,679 A | 5/1993 | Li | |
| 5,209,753 A * | 5/1993 | Biedermann et al. | 606/304 |
| 5,236,445 A | 8/1993 | Hayhurst et al. | |
| 5,261,909 A | 11/1993 | Sutterlin et al. | |
| 5,360,431 A | 11/1994 | Puno et al. | |
| 5,411,522 A | 5/1995 | Trott | |
| 5,472,452 A | 12/1995 | Trott | |
| 5,474,555 A | 12/1995 | Puno et al. | |
| 5,480,403 A | 1/1996 | Lee et al. | |
| 5,489,210 A | 2/1996 | Hanosh | |

(Continued)

FOREIGN PATENT DOCUMENTS

| | | |
|---|---|---|
| EP | 0129442 | 12/1984 |
| EP | 0574707 | 12/1993 |

(Continued)

OTHER PUBLICATIONS

Franklin, I.J. et al., "Uptake of Tetracycline by Aortic Aneurysm Wall and Its Effect on Inflammation and Proteolysis," *Brit J. Surger*, 86(6):771-775, 1999.

(Continued)

*Primary Examiner* — Nicholas Woodall
(74) *Attorney, Agent, or Firm* — Levine Bagade Han LLP

(57) ABSTRACT

An attachment device with a radially expandable section is disclosed. The attachment device can have helical threads, for example, to facilitate screwing the attachment device into a bone. Methods of using the same are also disclosed. The attachment device can be positioned to radially expand the expandable section in cancellous bone substantially surrounded by cortical bone.

22 Claims, 24 Drawing Sheets

(56) References Cited

U.S. PATENT DOCUMENTS

| | | |
|---|---|---|
| 5,501,695 A | 3/1996 | Anspach, Jr. et al. |
| 5,522,844 A | 6/1996 | Johnson |
| 5,643,321 A | 7/1997 | McDevitt |
| 5,649,950 A | 7/1997 | Bourne et al. |
| 5,662,654 A | 9/1997 | Thompson |
| 5,709,708 A | 1/1998 | Thal |
| 5,749,899 A | 5/1998 | Bardin |
| 5,782,866 A | 7/1998 | Wenstrom, Jr. |
| 5,797,963 A | 8/1998 | McDevitt |
| 5,824,011 A | 10/1998 | Stone et al. |
| 5,849,004 A | 12/1998 | Bramlet |
| 5,882,350 A | 3/1999 | Ralph et al. |
| 5,935,129 A | 8/1999 | McDevitt et al. |
| 6,146,406 A | 11/2000 | Shluzas et al. |
| 6,168,597 B1 | 1/2001 | Biedermann et al. |
| 6,200,330 B1 | 3/2001 | Benderev et al. |
| 6,224,604 B1 | 5/2001 | Suddaby |
| 6,319,255 B1* | 11/2001 | Grundei et al. ............ 606/76 |
| 6,458,100 B2 | 10/2002 | Roue et al. |
| 6,506,051 B2 | 1/2003 | Levisman |
| 6,585,770 B1 | 7/2003 | White et al. |
| 6,648,893 B2* | 11/2003 | Dudasik ............... 606/327 |
| 6,652,561 B1 | 11/2003 | Tran |
| 7,097,648 B1 | 8/2006 | Globerman et al. |
| 2002/0049447 A1* | 4/2002 | Li ....................... 606/73 |
| 2002/0165544 A1 | 11/2002 | Perren et al. |
| 2004/0138707 A1 | 7/2004 | Greenhalgh |
| 2005/0065526 A1* | 3/2005 | Drew et al. ............ 606/72 |
| 2005/0143827 A1 | 6/2005 | Globerman et al. |
| 2005/0187555 A1* | 8/2005 | Biedermann et al. ....... 606/72 |
| 2005/0228391 A1 | 10/2005 | Levy et al. |
| 2006/0015104 A1 | 1/2006 | Dalton |
| 2006/0052788 A1 | 3/2006 | Thelen et al. |
| 2006/0084987 A1 | 4/2006 | Kim |
| 2006/0190090 A1 | 8/2006 | Plaskon |
| 2006/0224241 A1 | 10/2006 | Butler et al. |
| 2006/0235391 A1 | 10/2006 | Sutterlin |
| 2006/0264950 A1 | 11/2006 | Nelson et al. |
| 2006/0271061 A1 | 11/2006 | Beyar et al. |
| 2007/0032791 A1 | 2/2007 | Greenhalgh |
| 2007/0093899 A1* | 4/2007 | Dutoit et al. ............ 623/17.11 |
| 2007/0198018 A1* | 8/2007 | Biedermann et al. ........... 606/73 |
| 2007/0282443 A1 | 12/2007 | Globerman et al. |
| 2008/0288003 A1* | 11/2008 | McKinley ................... 606/313 |

FOREIGN PATENT DOCUMENTS

| | | |
|---|---|---|
| JP | 4-502567 | 5/1992 |
| JP | 11-504550 | 4/1999 |
| JP | 2002-514935 | 5/2002 |
| WO | WO 95/25469 | 9/1995 |
| WO | WO 00/44319 | 8/2000 |
| WO | WO 00/44321 | 8/2000 |
| WO | WO 00/44946 | 8/2000 |
| WO | WO 01/54598 | 8/2001 |
| WO | WO 03/003951 | 1/2003 |
| WO | WO 03/047440 | 6/2003 |
| WO | WO 2005/034764 | 4/2005 |
| WO | WO 2005/096975 | 10/2005 |
| WO | WO 2006/034396 | 3/2006 |
| WO | WO 2006/034436 | 3/2006 |
| WO | WO 2006/037013 | 4/2006 |
| WO | WO 2006/068682 | 6/2006 |
| WO | WO 2006/116760 | 11/2006 |
| WO | WO 2006/116761 | 11/2006 |
| WO | WO 2006/126979 | 11/2006 |
| WO | WO 2007/041665 | 4/2007 |
| WO | WO 2007/065137 | 6/2007 |
| WO | WO 2007/076374 | 7/2007 |
| WO | WO 2007/076377 | 7/2007 |

OTHER PUBLICATIONS

Pyo, R. et al., "Targeted Gene Disruption of Matrix Metalloproteinase-9 (Gelatinase B) Suppresses Development of Experimental Abdominal Aortic Aneurysms," *J. Clinical Investigation*, 105(11):1641-1649, Jun. 2000.

Tambiah, J. et al., "Provocation of Experimental Aortic Inflammation Mediators and Chlamydia Pneumoniae," *Brit., J. Surgery*, 88(7):935-940, Feb. 2001.

Walton, L.J. et al., "Inhibition of Prostoglandin E2 Synthesis in Abdominal Aortic Aneurysms," *Circulation*, 48-54, Jul. 6, 1999.

Xu, Q. et al., "Sp1 Increases Expression of Cyclooxygenase-2 in Hypoxic Vascular Endothelium," *J. Biological Chemistry*, 275(32):24583-24589, Aug. 2000.

* cited by examiner

NOT INVENTION

NOT INVENTION

NOT INVENTION

NOT INVENTION

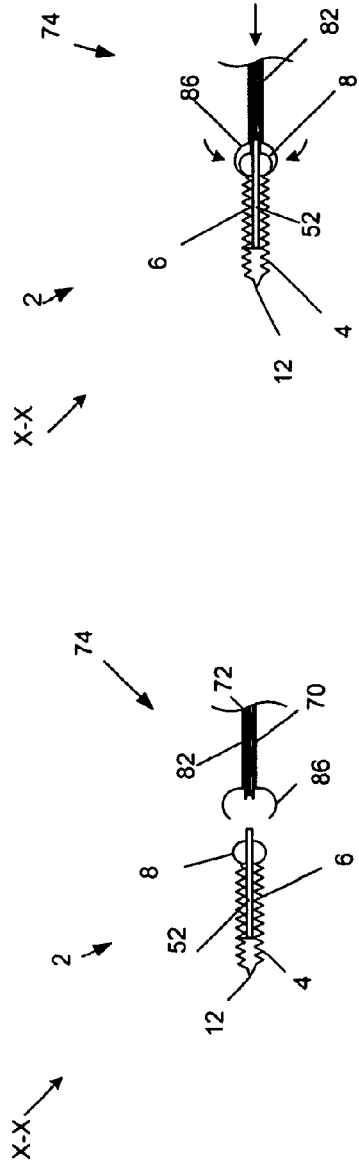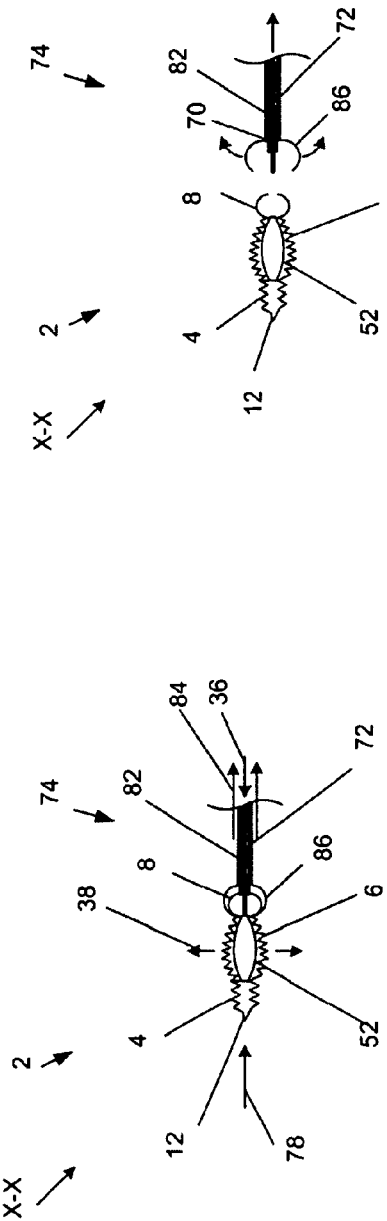

NOT INVENTION

NOT INVENTION

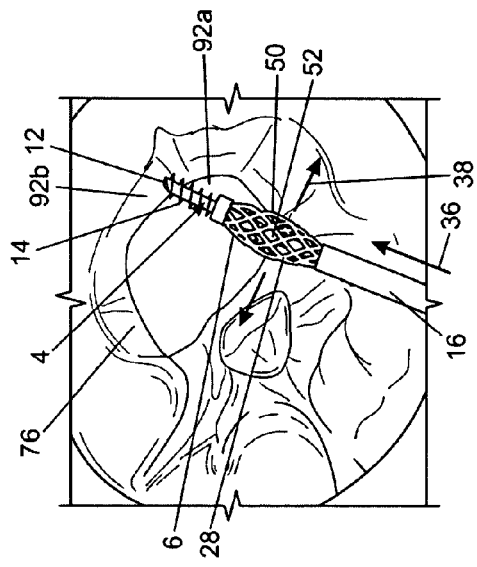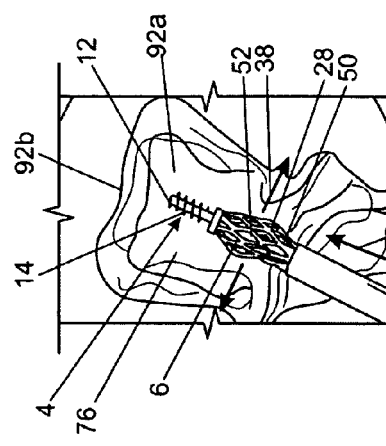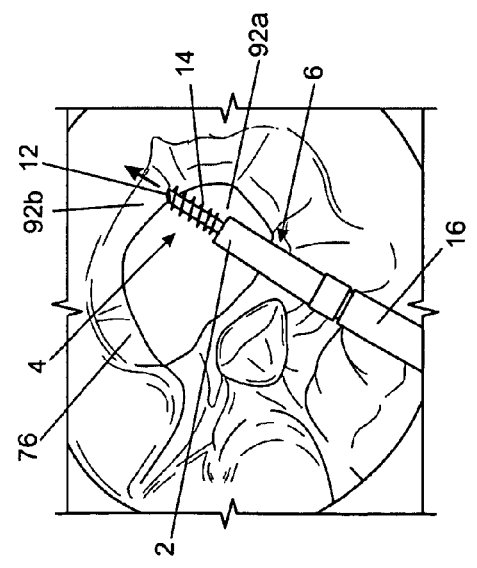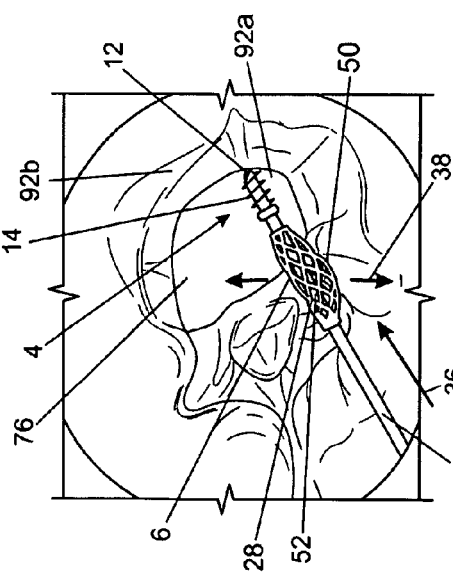

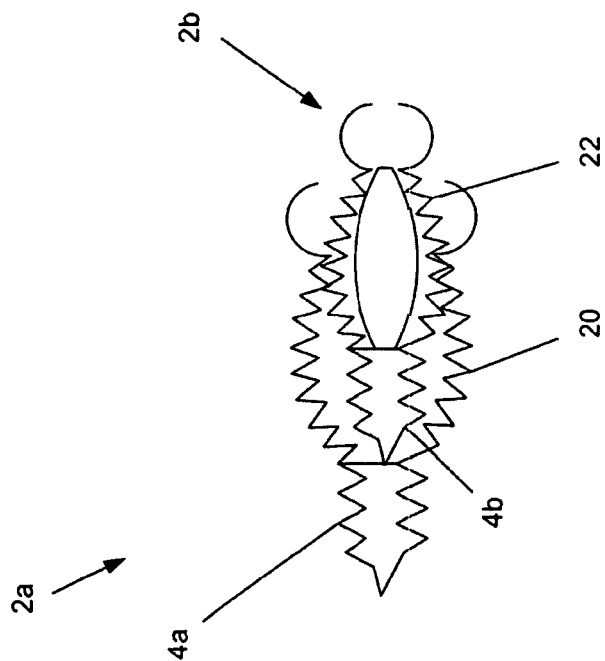

EXPANDABLE ATTACHMENT DEVICE AND METHOD

CROSS REFERENCE TO RELATED APPLICATIONS

This application claims the benefit of U.S. Provisional Application No. 60/985,087, filed Nov. 2, 2007, which is incorporated by reference herein in its entirety.

BACKGROUND OF THE INVENTION

1. Field of the Invention

The present invention relates generally to a device and method for attaching to bones.

2. Description of Related Art

Broken bones, such as compression fractures of one or more vertebrae in the spine, may be treated with internal fixation. Any indication needed spinal stability can also be treated by internal fixation. Examples include scoliosis, kyphosis, spondylothisthesis and rotation, segmental instability, such as disc degeneration and fracture caused by disease and trauma and congenital defects, and degeneration caused by tumors.

As shown by FIG. 1, internal fixation in the spine is often accomplished by first screwing fixation screws 200 into the pedicles and vertebral bodies of the vertebrae 88. FIG. 2 shows that the fixation screws 200 are then typically attached to a rigid fixation rod or plate 94 that provides support between one or more weakened vertebra 88. This support often immobilizes the vertebra 88 to which the fixation screws 200 have been inserted.

FIG. 3 illustrates that existing fixation systems often have the fixation rod or plate 94, through which a number of fixation screws 200 are deployed. The screw head 202 prevents the fixation rod 88 from separating from the fixation screw 200. The fixation screw 200 also has a screw body 204 which has a screw longitudinal axis 206 often static relative to the fixation rod 94.

FIG. 4 illustrates that in some existing fixation systems, the fixation screws 200 can be polyaxial screws: attached to the fixation rod or plate 94 in a manner so that the screw longitudinal axis 206 can rotate, as shown by arrows, with respect to the fixation rod 94.

Backing out or loosening of the fixation screws can cause a reduction of the fixation, up to complete failure or even resulting in additional complications.

Furthermore, the bones are often weak and under heavy loads, the bones can fail and the fixation screws can be ripped from the bone resulting in complete failure and additional damage to the bone.

Therefore, a fixation screw that can substantially eliminate the risk of backout, and can provide a higher anchoring force is desired. A fixation screw that can also minimize bone failure is desired.

SUMMARY OF THE INVENTION

An expandable attachment device and methods for using the same are disclosed. The expandable attachment device can have a radially expandable section and a distal end. The distal end can be configured to be attached to a separate device, such as a fixation rod or plate. The device can have an unexpandable section.

Also disclosed is an expandable attachment device that can have a radially expandable section and an unexpandable section. The unexpandable section and/or the radially expandable section can have external threads.

The devices described herein can be used as substitutes for fixation screws in existing fixation systems. The devices can be used to treat broken bones, scoliosis, kyphosis, spondylothisthesis and rotation, segmental instability, such as disc degeneration and fracture caused by disease and trauma and congenital defects, and degeneration caused by tumors.

The devices can be configured to be used in systems with fixed screw longitudinal axis or polyaxial configurations.

BRIEF DESCRIPTION OF THE DRAWINGS

FIGS. 31a through 31d illustrate cross-section X-X of FIG. 29 for a variation of a method for using a variation of the deployment tool and expandable attachment device.

FIGS. 42 through 44 are visualization images of a variation of a method for using the expandable attachment device.

FIG. 45 is a lateral view of FIG. 44.

FIG. 50 illustrates a method for deploying multiple expandable attachment devices.

DETAILED DESCRIPTION OF THE INVENTION

Figure 1:
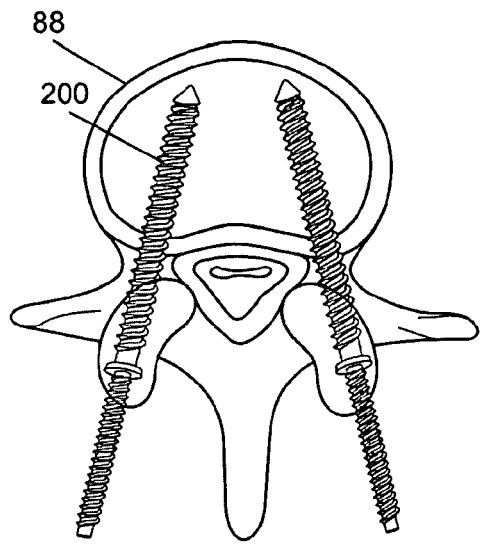
FIG. 1 is a partially see-through top view of a vertebra with fixation screws therethrough.
Figure 2:
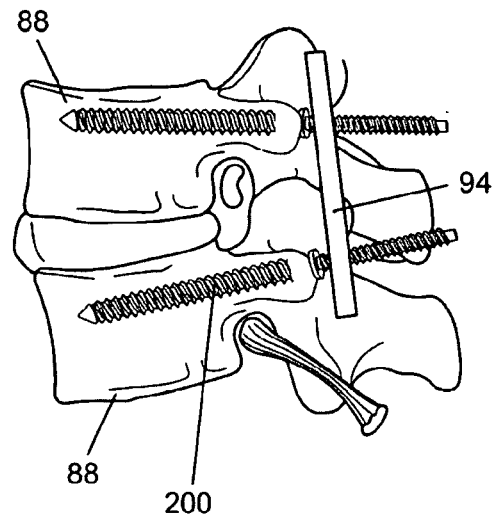
FIG. 2 is a partially see-through lateral view of a section of the spine with fixation screws and a fixation rod.
Figure 3:
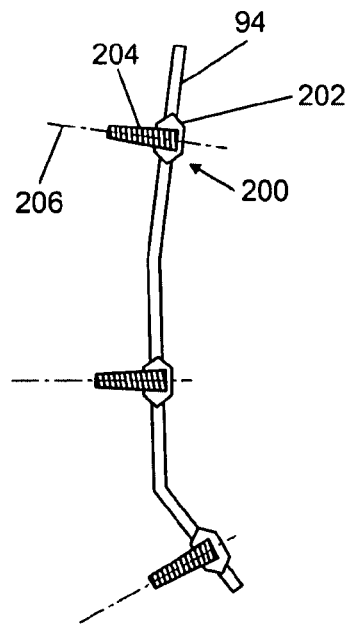
FIGS. 3 and 4 illustrate simplified variations of existing fixation systems.
Figure 4:
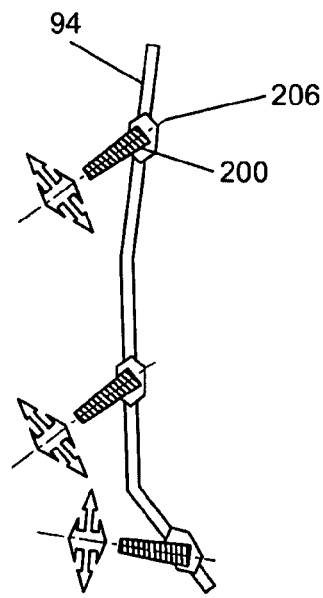
Figure 5:
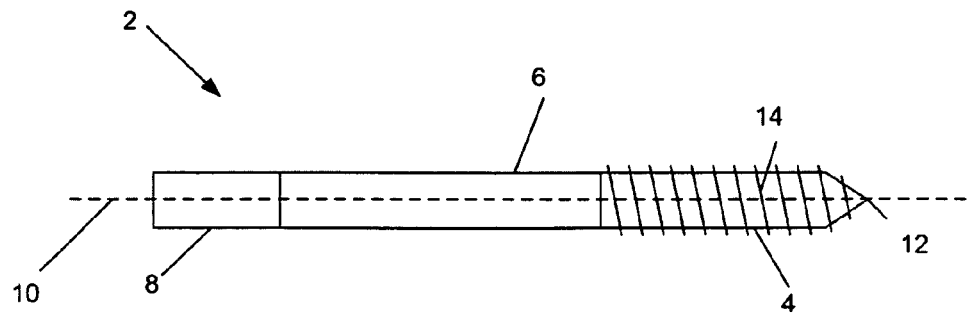
FIG. 5 illustrates a variation of the expandable attachment device in a radially contracted configuration.

FIG. 5 illustrates that the expandable attachment device 2 can have an unexpandable section 4 at a proximal end, an expandable section 6 at a medial length along the expandable attachment device 2, and a distal end 8. In other variations of the expandable attachment device 2, the unexpandable section 4 can be distal to the expandable section 6, and/or the expandable attachment device 2 can have more than one expandable section 6 and/or unexpandable section 4 that can be interspersed with each other.

The expandable attachment device 2 can have an expandable attachment device axis 10. The expandable device axis can be substantially straight.

The proximal end of the expandable attachment device 2 can have a tip 12. The tip 12 can be sharpened or otherwise configured to seat the expandable attachment device 2 in bone (e.g., having cutting teeth). The unexpandable section 4 can have unexpandable thread 14, for example, configured to screw the expandable attachment device 2 into bone.

Figure 6:
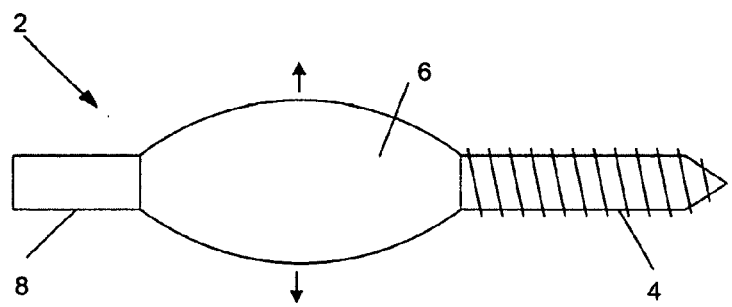
FIG. 6 illustrates the variation of the expandable attachment device in a radially expanded configuration.

FIG. 5 shows that the expandable attachment device 2 can have a radially contracted configuration. FIG. 6 illustrates that the expandable attachment device 2 can have a radially expanded configuration. For example, the expandable section 6 can be radially expanded, as shown by arrows.

The expandable section 6 can be resiliently and/or deformably expandable. The expandable sections 6 can be radially expanded by axial compression (e.g., see FIGS. 8-11), rotation (e.g., see FIGS. 26-29), use of a lever such as a wedge, ramp or jack (e.g., see FIGS. 58-64), or combinations thereof.

The expandable attachment device 2 can be substantially flat or planar.

The expandable section 6 can be biased to resiliently radially expand. For example, the expandable section 6 can be self-expandable or releasable spring. The expandable section 6 can be resiliently radially expandable and can be additionally deformably radially expandable to a larger radius than achieved by resilient expansion alone.

The expandable section 6 can have one or more anchors extending radially therefrom when the expandable section 6 is in the radially expanded configuration. The anchors can be brads, hooks, pins, teeth, fasteners, pegs, screws, skewers, spikes, stakes, or combinations thereof.

The expandable attachment device 2 can be configured to radially expand in volumetrically, for example to have radial expansion in two dimensions. The expandable attachment device 2 can be configured to radially expand planarly, for example, in a single dimension (i.e., to have radial expansion in only two substantially opposite directions).

Figure 7:
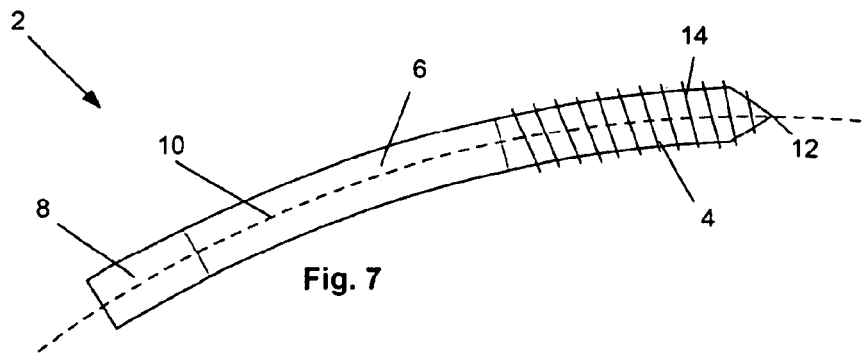
FIG. 7 illustrates a variation of the expandable attachment device in a radially contracted configuration.

FIG. 7 illustrates that the expandable attachment device axis 10 can be substantially curved or angled. The expandable attachment device axis 10 can have one or more curved, and/or angled, and/or straight lengths. For example, the expandable attachment device axis 10 can have a substantially straight length along the unexpandable section 4 and the distal end 8, and a curved length along the expandable section 6. The expandable attachment device axis 10 can have one or more curves with a constant or variable (i.e., changing along the length of the attachment device axis 10) radius of curvature and/or one or more abrupt and discrete non-zero angles.

When the expandable attachment device 2 is inserted in a bone, such as a vertebra, the expandable attachment device 2 can follow a longitudinal axis of insertion that is straight, curved, or a combination thereof. For example, the expandable attachment device 2 can follow a longitudinal axis of insertion through the bone that is substantially similar in shape to the expandable attachment device axis 10.

Figure 8:
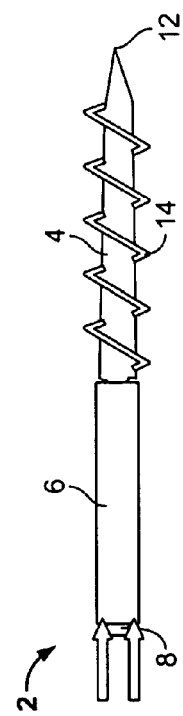
FIGS. 8 and 9 illustrate a variation of the expandable attachment device and a method for radially expanding the device.
Figure 9:
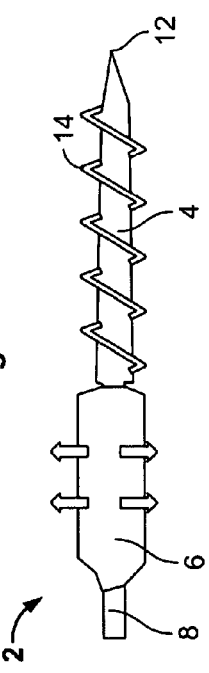

FIGS. 8 and 9 illustrates that the expandable attachment device 2 can be radially expanded by applying a proximally-directed force to the distal end 8 as shown by arrows of FIG. 8. The proximally-directed force can be substantially parallel to the expandable attachment device axis 10. The proximal force can be opposed by a distal force applied, for example, by the bone and/or a deployment tool 16. The expandable section 6 can then radially expand, as shown by arrows in FIG. 9.

Figure 10:
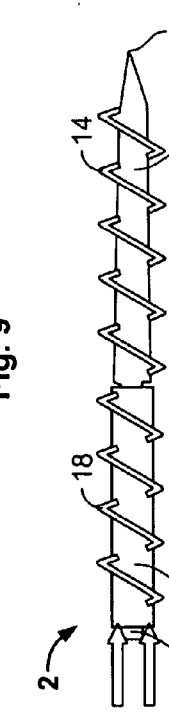
FIGS. 10 and 11 illustrate a variation of the expandable attachment device and a method for radially expanding the device.
Figure 11:
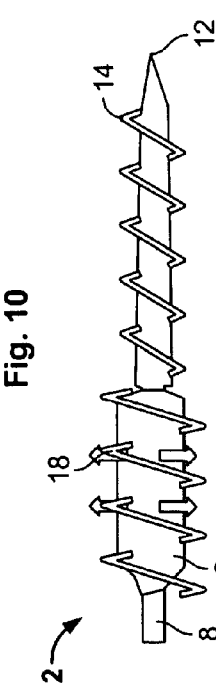

FIGS. 10 and 11 illustrate that the expandable attachment device 2 can have expandable thread 18 on the expandable section 6 and unexpandable thread 14 on the unexpandable section 4. The expandable thread 18 can radially expand with the remainder of the expandable section 14. The expandable attachment device 2 shown in FIGS. 10 and 11 can be radially expanded by the method as shown in FIGS. 8 and 9.

Figure 12:
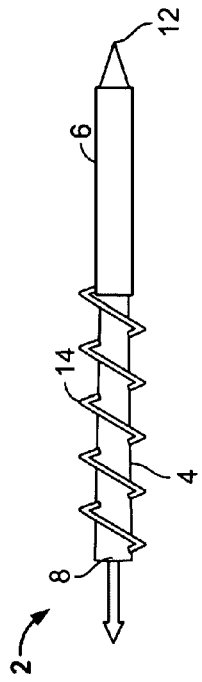
FIGS. 12 and 13 illustrate a variation of the expandable attachment device and a method for radially expanding the device.
Figure 13:
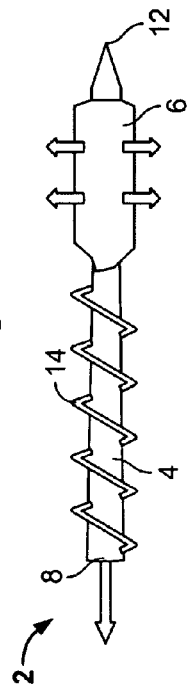

FIGS. 12 and 13 illustrate that the expandable attachment device 2 can be radially expanded by applying a distally-directed force to the distal end 8 as shown by arrow. The distally-directed force can be substantially parallel to the expandable attachment device axis 10. The distal force can be opposed by a proximal force applied, for example, by the bone and/or a deployment tool 16. The expandable section 6 can then radially expand, as shown by arrows in FIG. 13.

Figure 14:
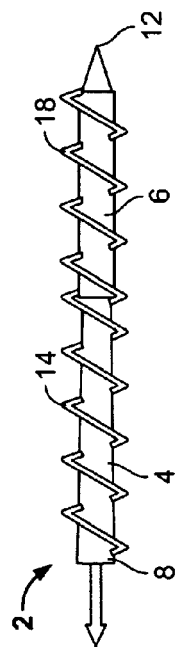
FIGS. 14 and 15 illustrate a variation of the expandable attachment device and a method for radially expanding the device.
Figure 15:
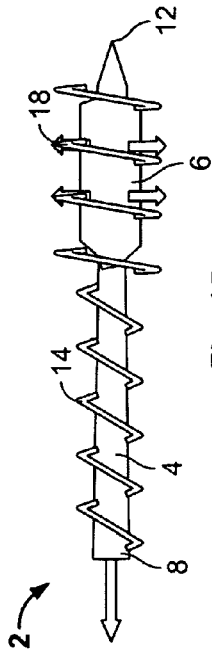

FIGS. 14 and 15 illustrate that the expandable attachment device 2 can have expandable thread 18 on the expandable section 6 and unexpandable thread 14 on the unexpandable section 4. The expandable thread 18 can radially expand with the remainder of the expandable section 6. The expandable attachment device 2 shown in FIGS. 14 and 15 can be radially expanded by the method as shown in FIGS. 12 and 13.

Figure 16:
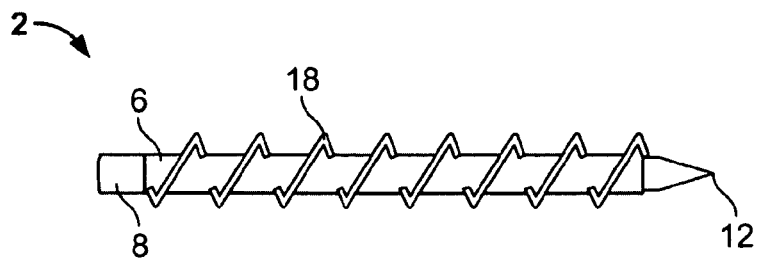
FIGS. 16 and 17 illustrate a variation of the expandable attachment device and a method for radially expanding the device.
Figure 17:
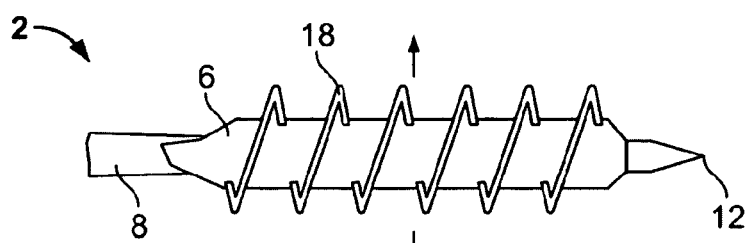
Figure 18:
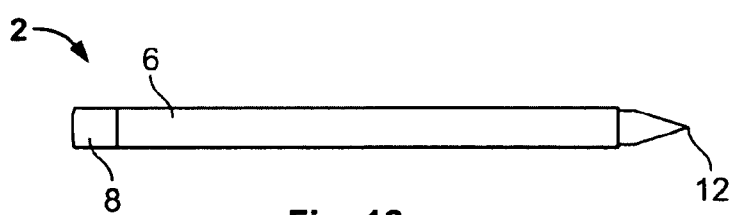
FIG. 18 illustrates a variation of the expandable attachment device in a contracted configuration.
Figure 19:
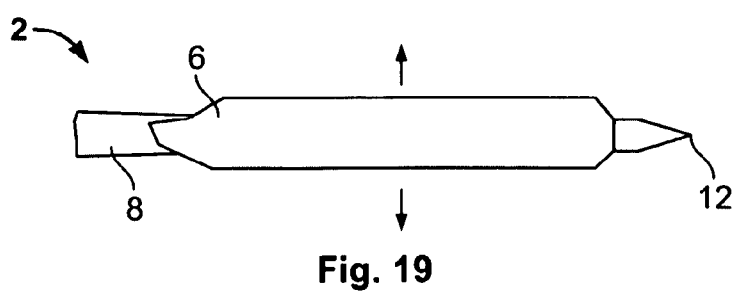
FIGS. 19 and 20 illustrate variations of the expandable attachment device of FIG. 18 and methods for radially expanding the device.

FIG. 16 illustrate that substantially the entire length of the expandable attachment device 2 can be the expandable section 6. The distal end can extend distally from the expandable section 6. FIG. 17 illustrates that the entire expandable section 6 can radially expand. FIGS. 16 and 17 illustrate that the expandable section 6 can have expandable thread 18. FIGS. 18 and 19 illustrate the variation of the expandable attachment device 2 of FIGS. 16 and 17, respectively, without expandable thread 18.

Figure 20:
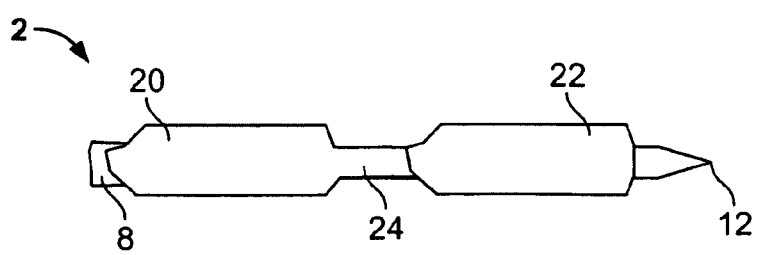

FIG. 20 illustrates that the expandable attachment device 2 can have, from distal to proximal, a first expandable section 20, a third expandable section 24, and a second expandable section 26. The first, second and third expandable sections 20, 22, 24 can radially expand at different rates (e.g., under different deployment loads, for example one or more are resiliently and one or more are deformably expandable). For example, the first and second expandable sections 20, 22 can radially expand at the same rate, and the third expandable section 24 can radially expand at a lesser rate.

Figure 21:
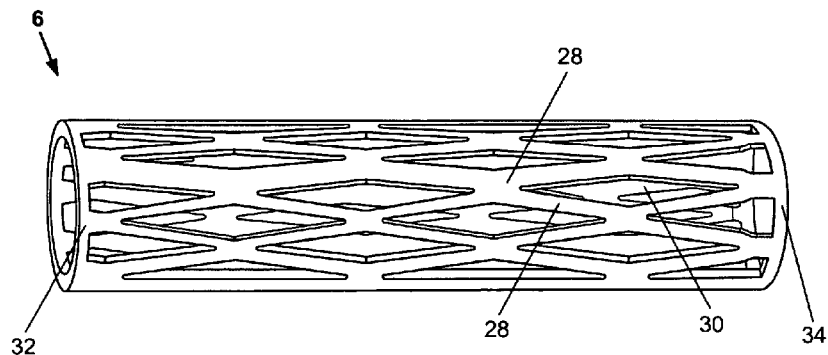
FIG. 21 illustrates a variation of the expandable section in a radially contracted configuration.

FIG. 21 illustrates that the expandable section 6 can have a number of struts 26 attached to each other at joints 28. When the expandable section 6 is in a radially contracted configuration, the struts 26 can be configured to form diamond-shaped ports 30. The expandable section 6 can have a distal hoop 32 at the distal end 8 and/or a proximal hoop 34 at the proximal end. The hoops can attach to all of the struts 26 at the respective end. The hoops and struts 26 can all be integral with and/or attached to each other.

Figure 22:
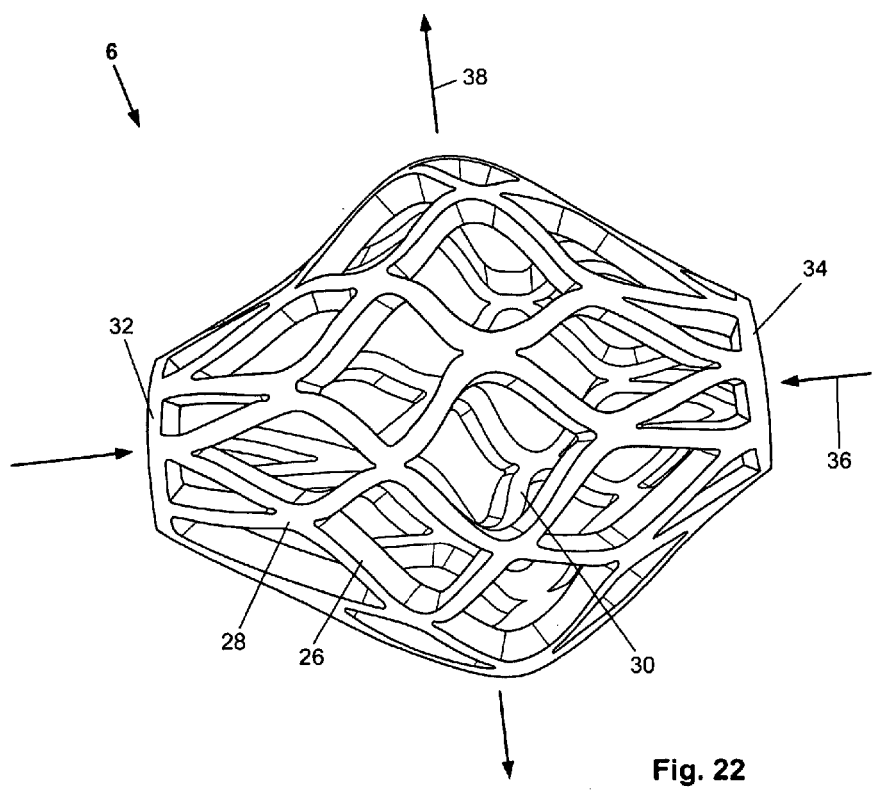
FIG. 22 illustrates the expandable section of FIG. 21 in a radially expanded configuration.

FIG. 22 illustrates that longitudinal compressive force, shown by arrow 36, can be applied to the expandable section 6, for example resulting in radial expansion, shown by arrows 38. In a radially expanded configuration, the struts 26 can deform near the joints 28. The hoops can remain substantially static.

Figure 23:
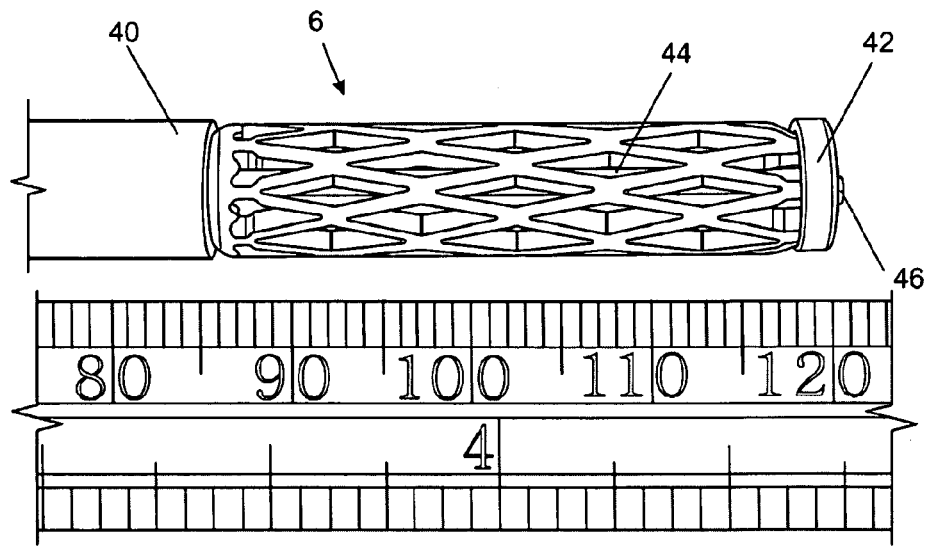
FIG. 23 illustrates a variation of the expandable section in a radially contracted configuration on the expandable attachment device.
Figure 24:
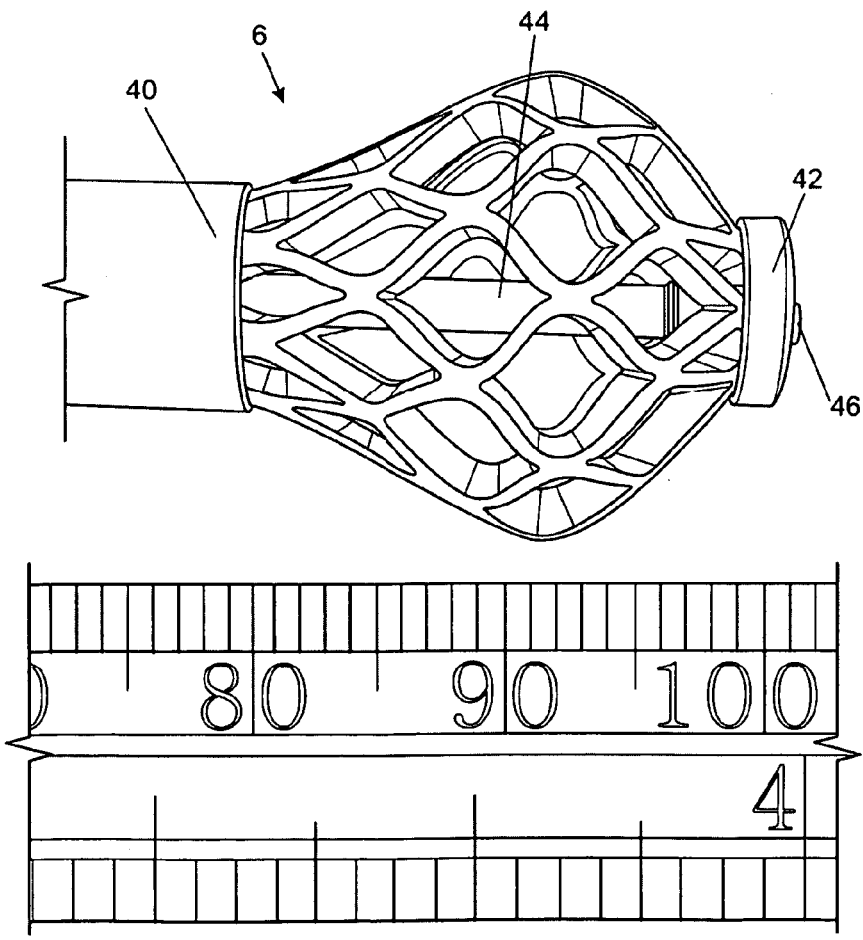
FIG. 24 illustrates a variation of the expandable section in a radially expanded configuration on the expandable attachment device.

FIGS. 23 and 24 illustrates that the expandable section 6 can be radially expanded by longitudinally compressing the expandable section 6. For example, the deployment tool 16 (or expandable attachment device 2) can have an anvil 40 and a deployment cap 42. The anvil 40 can be the distal end 8 and/or the unexpandable section 14. The deployment cap 42 can be the unexpandable section 14 and/or the distal end 8, for example, the opposite of the anvil 40. The expandable section can be compressed between the anvil 40 and the deployment cap 42.

The deployment tool 16 (or expandable attachment device 2) can have a deployment rod 44, for example to transmit the compressive force to the deployment cap 42. The deployment rod 44 can be releasably attached to the deployment cap 42, for example via a releasable deployment anchor 46. The releasable deployment anchor 46 can be released and the deployment rod 44 can be removed after the expandable section 6 is radially expanded.

Figure 25:
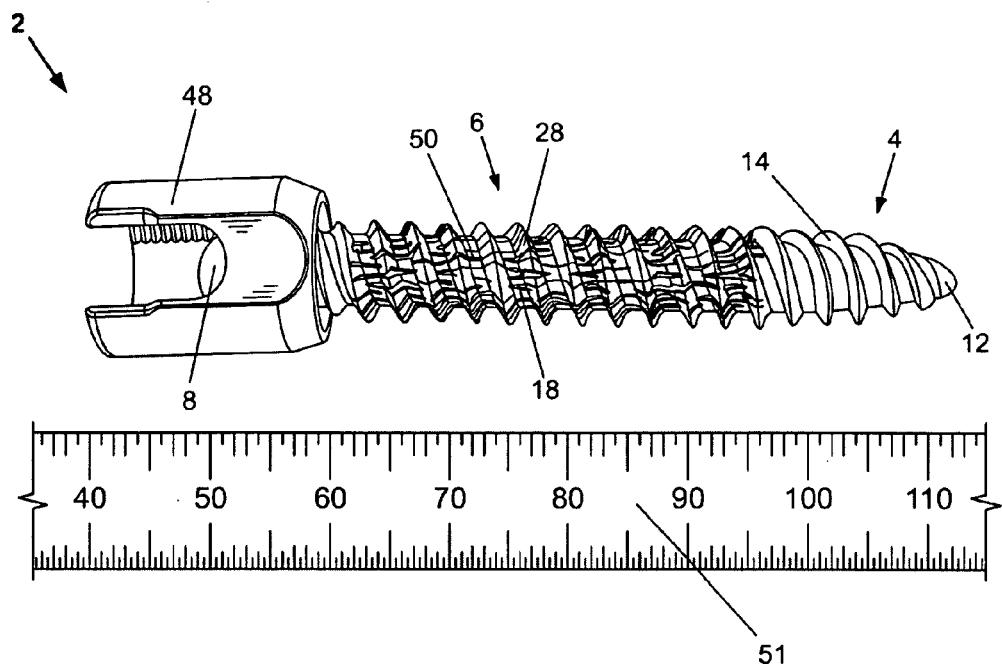
FIG. 25 illustrates a variation of the expandable attachment device in a radially contracted configuration.

FIG. 25 illustrates that the expandable attachment device 2 can have a fixation joint 48. The fixation joint 48 can be fixedly or removably attached to the expandable attachment device 2, for example interference fit with the distal end 8. The fixation joint 48 can be uniaxially or polyaxially rotatably (e.g., with one, two or three degrees or rotational freedom) and/or translatably attached to the expandable support device 2. The fixation joint 48 can be configured to attach to a fixation element, such as a rod or plate configured to substantially fix the bone into which the expandable attachment device 2 is inserted.

The cells 50 can be W-shaped, A-shaped, V-shaped, another configuration disclosed herein for cells 40, or combinations thereof. A single expandable section can have various cell 40 configurations.

A scale 51 is shown numbered in millimeters.

Figure 26:
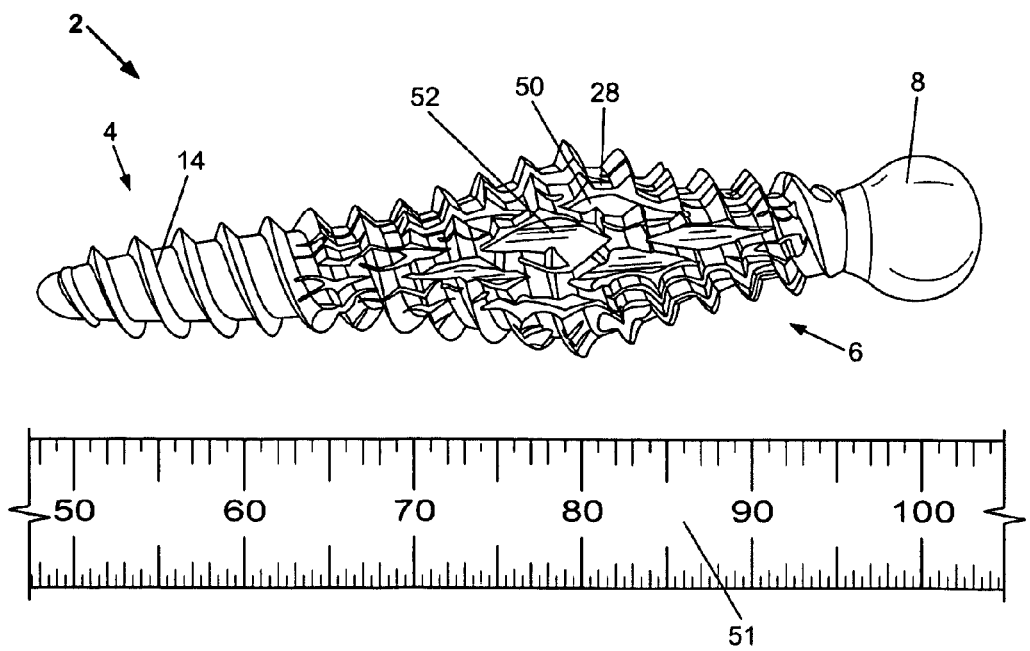
FIG. 26 illustrates a variation of the expandable attachment device in a radially expanded configuration.

FIG. 26 illustrates that the struts 26 can be in a radially expanded configuration. The cells can be in an opened configuration. The expander can be configured to be a radially non-expandable center shaft or radially expandable. The expandable attachment device 2 can be radially expanded, for example, by compressing the expander 52 and/or by longitudinally compressing the expandable attachment device 2.

The longitudinally distal end 8 can be removably or fixedly attached to a cap. The cap can be configured to attach to the fixation joint 48.

A scale 51 is shown numbered in millimeters.

Figure 27A:
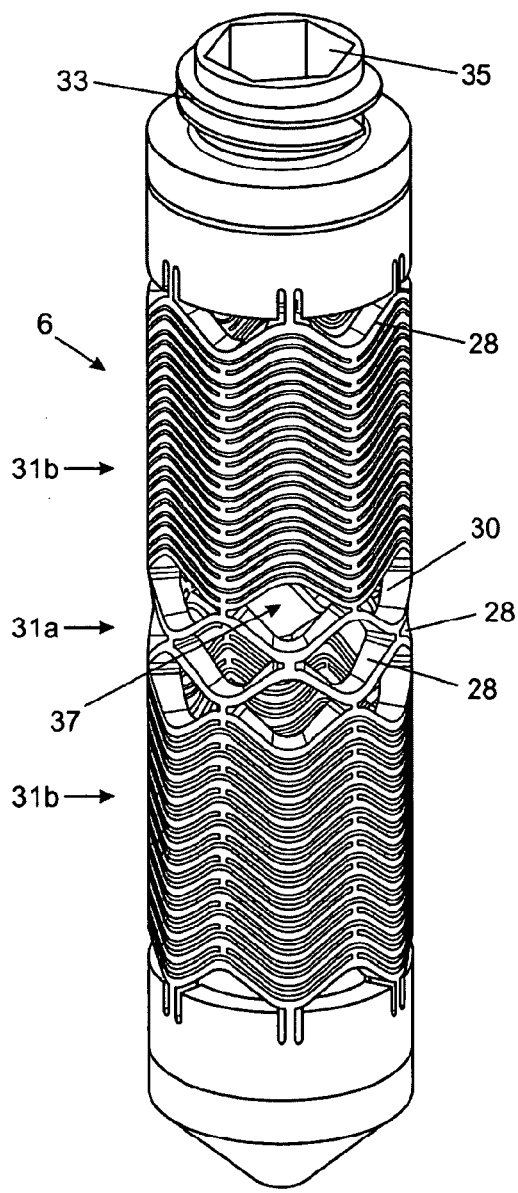
FIGS. 27a through FIG. 27e illustrate variations of the expandable section.

FIGS. 27a-e illustrate variations of the strut 26, port 30 and joint 28 configuration of the expandable section. FIG. 27a illustrates that the ports 30 can be larger near the longitudinal median or a central section 31a of the expandable section 6. The lengths of the expandable section 6 with larger ports 30, for example along the central section 31a, can radially expand during longitudinal compression 54 before the lengths of the expandable section 6 with smaller ports 30, for example along the end regions 31b.

The expandable attachment device 2 can have an engagement configuration, such as thread 33, that can be configured to removably attach to a deployment tool. The engagement configuration can be at or near the proximal end of the expandable support device 2. The engagement configuration can have a tool port 35. The tool port 35 can be configured to engage a deployment tool, for example a hex key or Allen wrench. The tool port 35 can be an open port. The tool port 35 can provide access through the proximal end of the expandable support device into the central channel 37 of the expandable support device. For example, filler can be deployed through the tool port 35 and into the central channel 37. Filler can then exit from the central channel 37 through the cells or side ports 30 and, for example, into the cancellous bone surrounding the device 2.

Figure 27B:
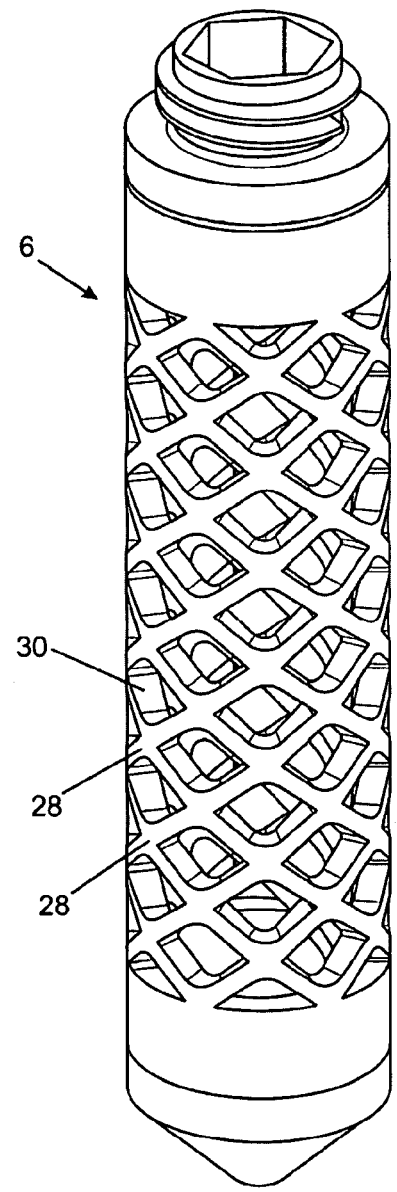
Figure 27C:
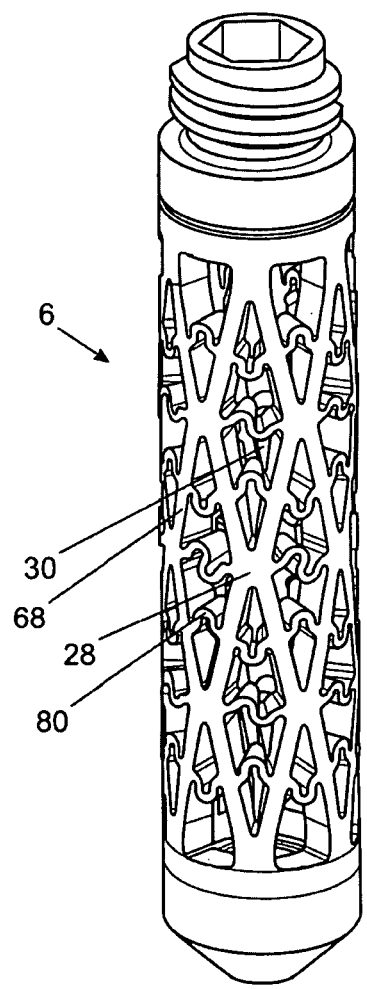
Figure 27D:
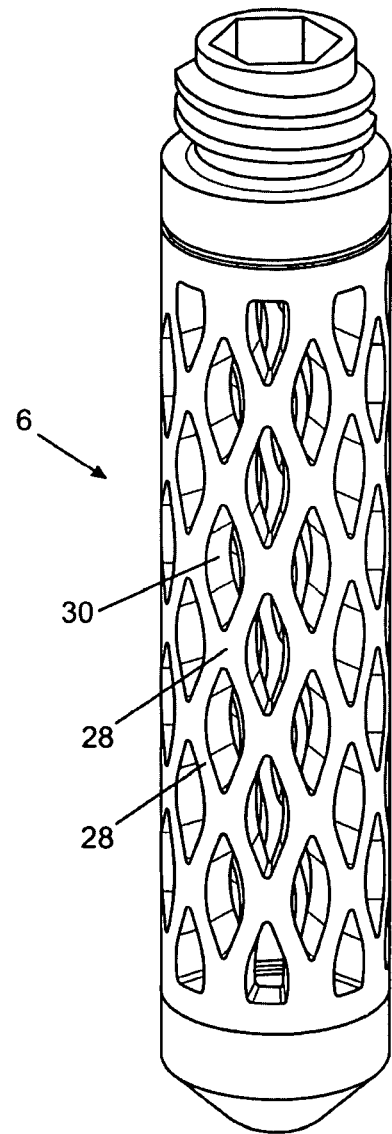
Figure 27E:
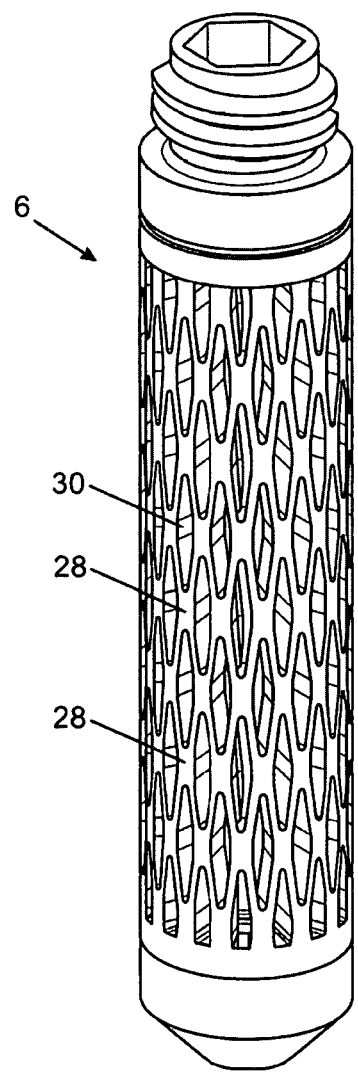

FIG. 27b illustrates that the struts 26 and ports 30 can be substantially identical along the entire length of the expandable section 6. FIG. 27c can have main struts 68 and smaller folded cross-struts 80 that attach to multiple main struts 68. FIG. 27d illustrates that the struts 26 and ports 30 can be substantially identical along the entire length of the expandable section 6 and that the ports 30 can be longer in the longitudinal direction that in the angular direction, with respect to the expandable section 6. FIG. 27e that the struts 26 and ports 30 can be substantially identical along the entire length of the expandable section 6 and that the ports 30 can be longer in the longitudinal direction that in the angular direction, with respect to the expandable section 6, and smaller and more numerous than as shown in FIG. 27d.

Figure 28:
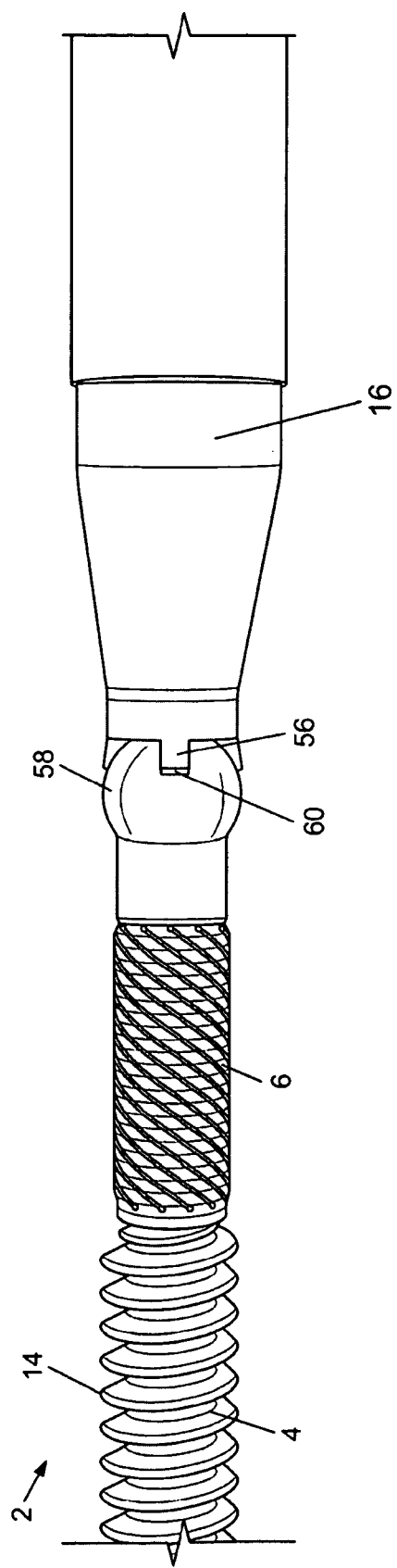
FIG. 28 illustrates a variation of the expandable attachment device attached to a variation of the deployment tool.

FIG. 28 illustrates that the expandable attachment device 2 can be releasably attached to the deployment tool 16. The deployment tool 16 can have deployment engagement teeth 56 that can align and intersect with the distal end cap 58, for example at the cap deployment tool attachments 60.

Figure 29:
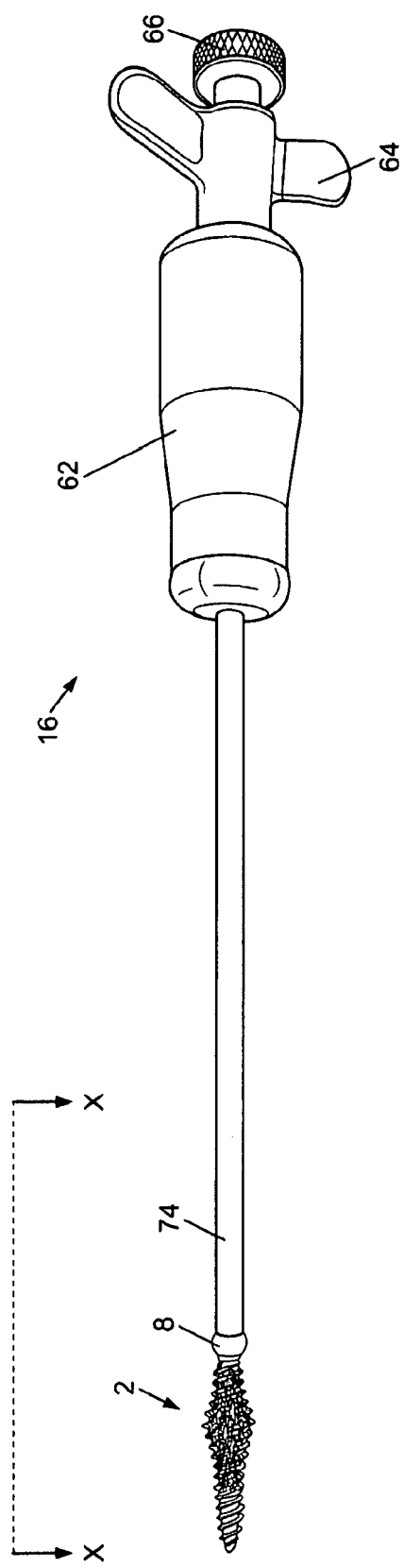
FIG. 29 illustrates a variation of the deployment tool attached to a variation of the expandable attachment device.

FIG. 29 illustrates that the deployment tool 16 can have a first tool handle 62, a second tool handle 64, a third tool handle 66, or combinations thereof. The tool handles 62, 64, 66 can be independently or jointly attached to, and configured to control, one or more tools within, attached or attachable to the deployment tool 16, such as a mechanical driver (e.g., screw driver 70, expander driver 72, holder, or combinations thereof) or a valve or power control for controlling the flow of a filler material or saline, or for operating a visualization or electrocautery or RF device. The tool handles can be configured to provide mechanical stability for the deployment tool 16.

The tool handles can be configured to ratchet (i.e., unidirectional movement or substantially free unidirectional motion with safety-controlled bidirectional motion). The tool handles can be configured to control rotation and translation or screwing of the expandable attachment device 2 into the target site. The tool handles can be configured to control the expandable attachment device 2 attachment to and release from the deployment tool 16. The tool handles can be configured to control the radial expansion 38 of the expandable attachment device 2.

The tool handles can be longitudinally translatable and/or rotatable. The tool handles can be configured for ergonomic use. The third tool handle 66 can have a knurled surface. The second tool handle 64 can have wings, for example configured as finger or thumb controls. The first tool handle 62 can have a configuration that is conical, cylindrical or combinations thereof.

The deployment tool 16 can have a tool shaft 74. The expandable attachment device 2 can be releasably attached to the tool shaft 74.

Figure 30B:
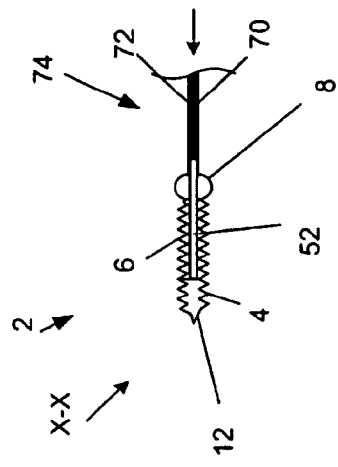
FIGS. 30a through 30d illustrate cross-section X-X of FIG. 29 for a variation of a method for using a variation of the deployment tool and expandable attachment device.
Figure 30D:
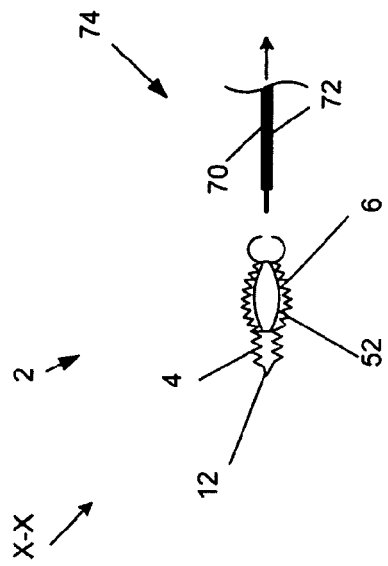
Figure 30A:
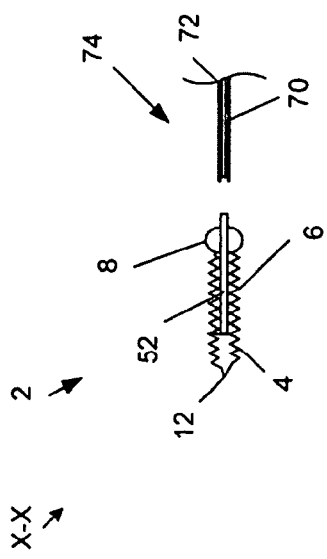

FIG. 30a illustrates that the tool shaft 74 can have an expander driver 72 and a screw driver 70. The terminal end of the tool shaft 74 can be aligned with the distal end 8 of the expandable attachment device 2.

FIG. 30b illustrates that the terminal end of the tool shaft 74 can be placed, as shown by arrow, in contact with the expandable attachment device 2. The screw driver 70 (e.g., the distal end of the deployment tool attachment) can releasably attach to or engage the distal end 8. The expander driver 72 can releasably attach to or engage the expander head (e.g., the expander deployment tool attachment). The deployment tool 16 can screw the expandable attachment device 2 into a target tissue site (e.g., a bone, such as vertebral body 76).

Figure 30C:
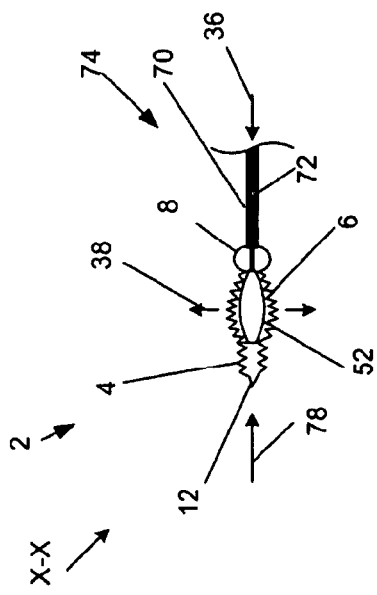

FIG. 30c illustrates that the expander driver 72 can deploy a longitudinal compressive force, shown by arrow 36, to the expander 52. The surrounding tissue can resist the longitudinal compressive force, as shown by in vivo resisting force arrow 78. The expander 52 fingers can radially expand, as shown by arrows 38. The expander 52 fingers can force the expandable section 6 (e.g., the struts 26) radially outward, as shown by arrows. The expandable attachment device 2 can be deformably or resiliently radially expanded.

FIG. 30d illustrates that the tool shaft 74 can be detached or disengaged and withdrawn from the expandable attachment device 2 and the target site.

FIG. 31a illustrates that the tool shaft 74 can have a holder shaft 82 terminating in one or more holder grips 86. The holder grips 86 can be rotatably attached to the holder shaft 82 at holder hinges. When the tool shaft 74 is aligned with and adjacent to the expandable attachment device 2, the holder grips 86 can be flexed or rotated radially outward. The holder grips 86 can be configured to attach to the distal end 8 of the expandable attachment device 2.

FIG. 31b illustrates that the terminal end of the tool shaft 74 call be placed, as shown by arrow, in contact with the expandable attachment device 2. When the tool shaft 74 is attached to or engaged with the expandable attachment device 2, the holder grips 86 can be flexed or rotated radially inward. The holder grips 86 can attach to the distal end 8 of the expandable attachment device 2.

FIG. 31c illustrates that the expander driver 72 can deploy a longitudinal compressive force 36, shown by arrow, to the expander 52. The surrounding tissue can resist the longitudinal compressive force 36, as shown by in vivo resisting force arrow 78, and/or the holder shaft 82 and holder grips 86 can pull, as shown by arrows 84, on the distal end 8 producing an external resisting force to oppose the longitudinal compressive force, as shown by arrow 36.

The expander 52 fingers can radially expand, as shown by arrows 38. The expander 52 fingers can force the expandable section 6 (e.g., the struts 26) radially outward, as shown by arrows. The expandable attachment device 2 can be deformably or resiliently radially expanded.

FIG. 31d illustrates that the holder grips 86 can flex or rotate radially outward, as shown by arrows. The holder grips 86 can detach or disengage from the distal end 8 of the expandable attachment device 2. The tool shaft 74 can be withdrawn from the expandable attachment device 2 and the target site.

The expandable attachment device 2 can be removed by reversing the deployment method. For example, the expander 52 and/or screw can be longitudinally pulled and expanded resulting in radial contraction of the expandable attachment device 2 (e.g., the struts 26). The expandable attachment device 2 can then be unscrewed or otherwise removed from the target site.

Figure 32:
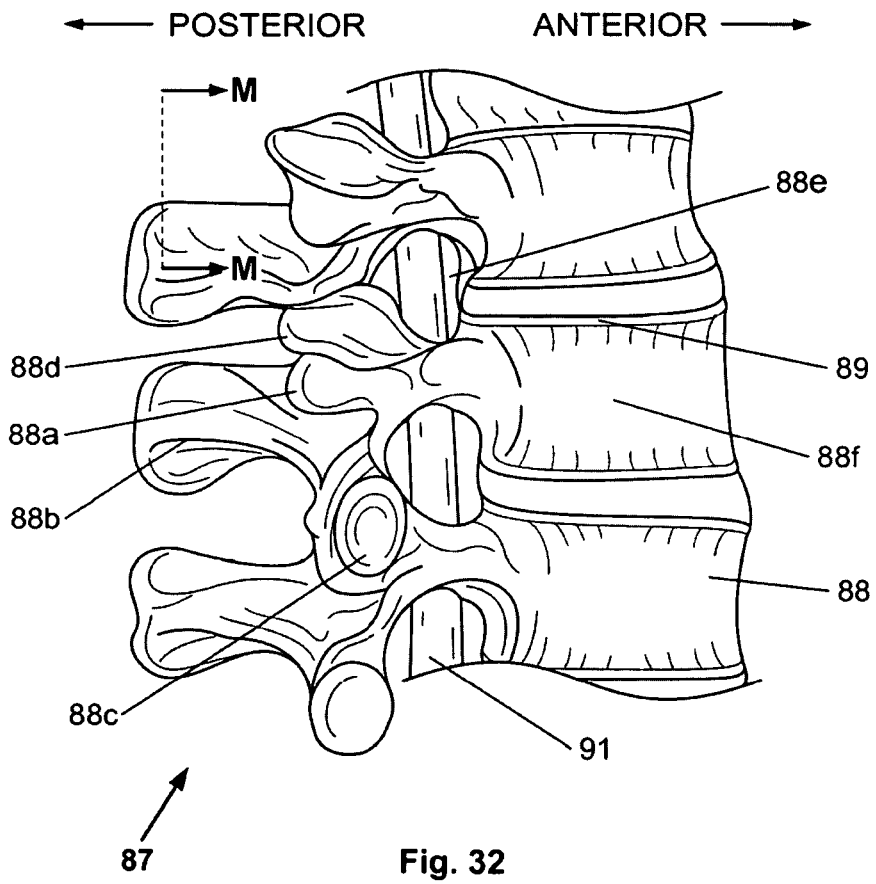
FIG. 32 is a lateral view of the spine.

FIG. 32 illustrates a side view of a spine 87. Vertebrae 88 within the spine 87 can have known anatomical features such as transverse processes 88a, spinous processes 88b, interior articular facets 88c, superior articular processes 88d, intervertebral foramen 88e, and vertebral bodies 88f. The spine 87 can also have intervertebral discs 89 and a spinal cord 91.

Figure 33:
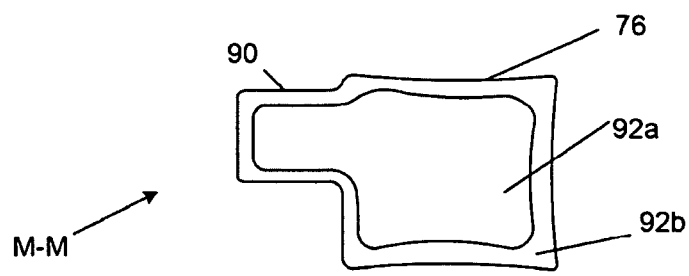
FIG. 33 illustrates cross-section M-M of FIG. 32.

FIG. 33 illustrates that harder, cortical bone 92b surrounds softer, cancellous bone 92a in the vertebra 88.

Figure 34:
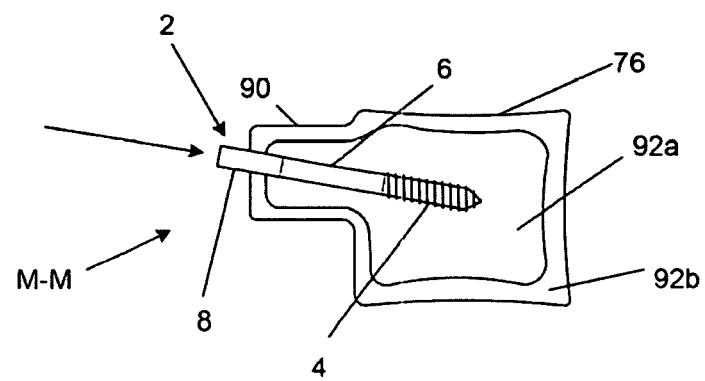
FIG. 34 illustrates cross-section M-M of FIG. 32 with an expandable attachment device delivered into the pedicle and/or vertebral body.

FIG. 34 illustrates that the expandable attachment device 2 can be translated and/or rotated into the pedicle 90 and/or into the vertebral body 76. The expanded section 6 can be positioned in the cortical bone 92b.

Figure 35:
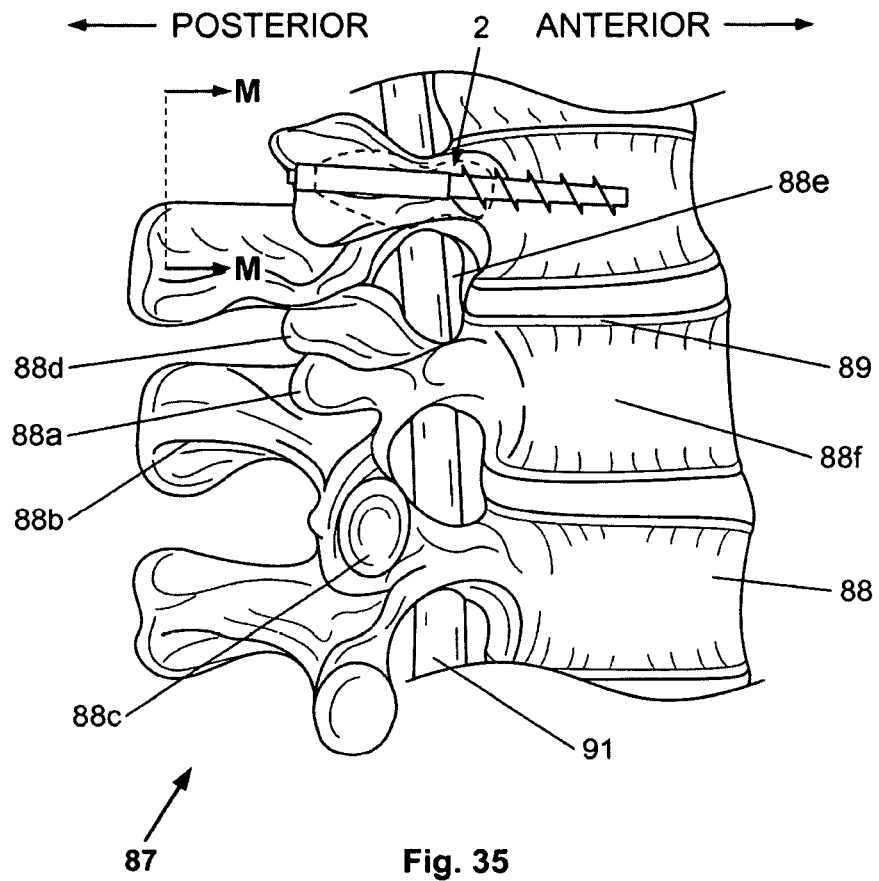
FIG. 35 is a partial see-through lateral view of the spine with a variation of the expandable attachment device delivered to, and radially expanded in, the pedicle and/or vertebral body.
Figure 36:
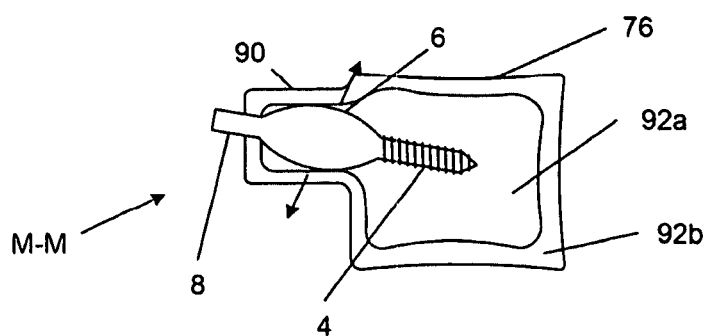
FIG. 36 illustrates cross-section M-M of FIG. 35.

FIGS. 35 and 36 illustrate that the expandable section 6 can be radially expanded, for example in the cancellous bone 92a of the pedicle 90 and/or the vertebral body 76. The radius of the radially expanded section 6 can be larger than the entry hole created to insert the attachment device 2 into the vertebra 88.

The distal end 8 can extend from the bone. A separate device, such as a fixation rod 94 or plate, can be attached to the distal end 8.

Figure 37:
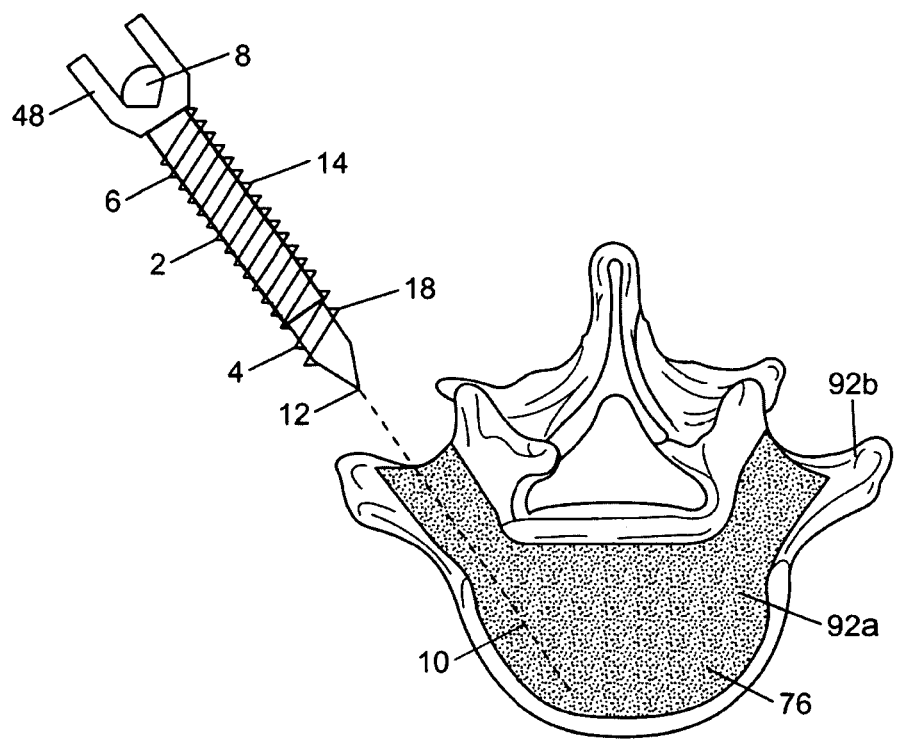
FIGS. 37 through 41 illustrate a variation of a method for using the expandable attachment device in a vertebral body.

FIG. 37 illustrates that the expandable attachment device 2 can be aligned with or adjacent to the pedicle 90 of the vertebral arch.

Figure 38:
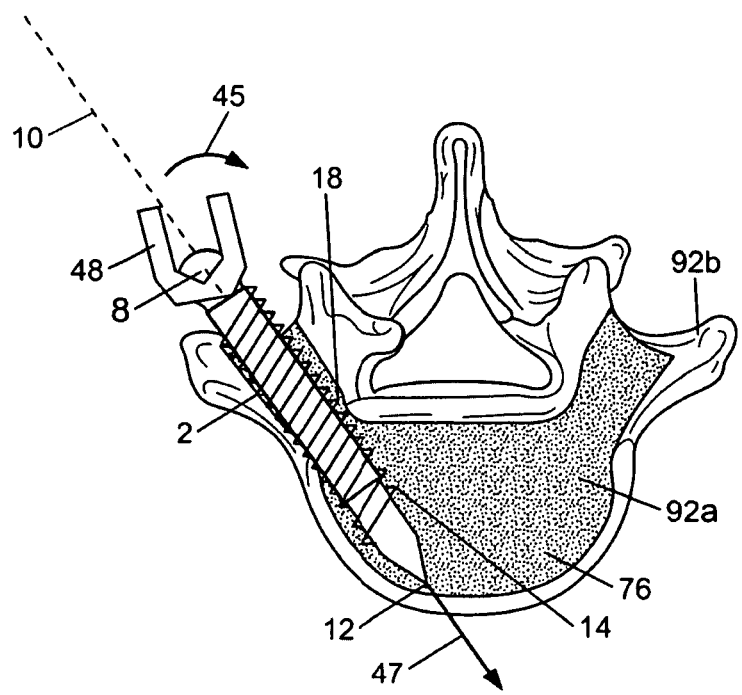

FIG. 38 illustrates that the expandable attachment device 2 can be screwed or otherwise inserted, as shown by arrow 47, into the vertebral body 76 through cortical bone 92b and cancellous bone 92a. The tip 12 can pierce the bone. The expandable thread 18 and unexpandable thread 14 can screw through the bone and anchor in the bone.

The fixation joint 48 can rotate, as shown by arrow 45, relative to the remainder of the expandable attachment device 2.

Figure 39:
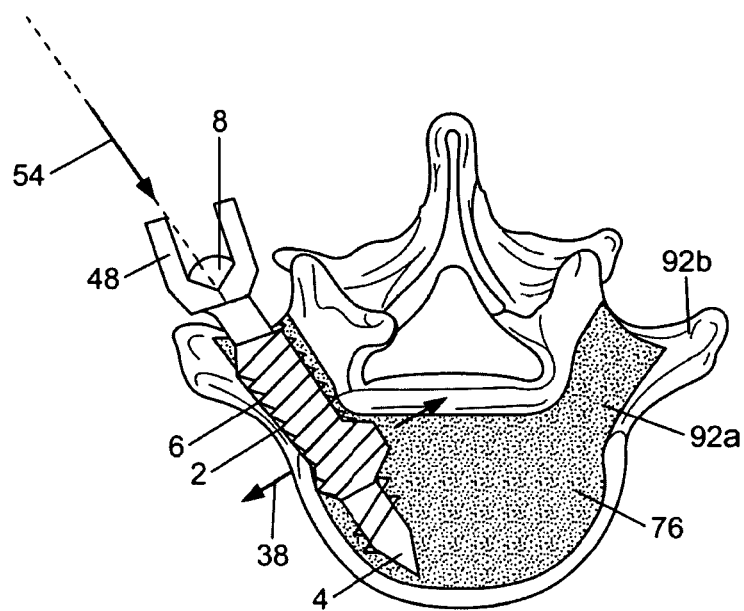

FIG. 39 illustrates that the expandable attachment device 2 and/or the expander can be longitudinally compressed, as shown by arrow 54. The longitudinal compression of the expandable attachment device 2 and/or the expander 52 can radially expand, as shown by arrows 38, the expandable section 6. The expandable section 6 can be configured to expand through the cancellous bone 92a and confirm to the cortical bone 92b during radial expansion.

Figure 40:
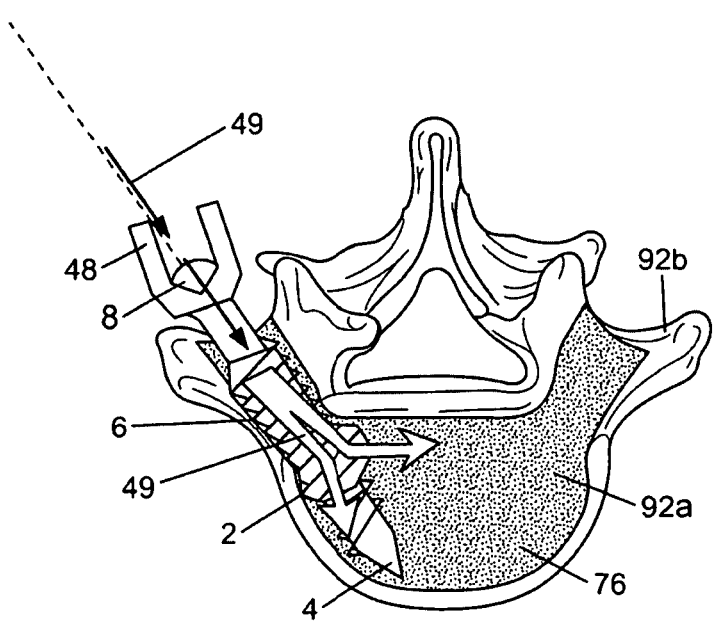

FIG. 40 illustrates that a filler 49, such as materials disclosed herein, can be deployed, as shown by arrows, through or adjacent to the expandable attachment device 2, for example through the open cells 50. The filler 49 can be a liquid, gel, small solid particles (e.g., morselized bone), or combinations thereof.

Figure 41:
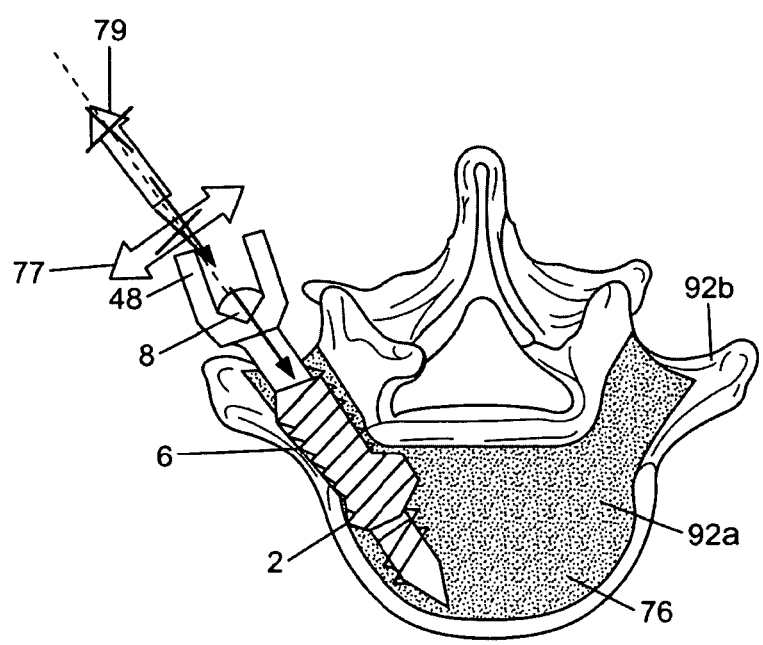

FIG. 41 illustrates that the fixation joint 48 can substantially partially minimize the transmission of excessive forces to the bone from the expandable attachment device 2 from. For example, the fixation joint 48 can rotate, as shown by arrow 77, about one or more axes. The fixation joint 48 can absorb, as shown by arrow 79, mechanical loads, for example by flexing, deforming, bending, and/or translating relatively small distances.

FIG. 42 illustrates that the expandable attachment device 2 can be screwed through cortical bone 92b and into the cancellous bone 92a of a vertebral body 76.

FIG. 43 illustrates that a longitudinal force can be applied by the deployment tool 16. The expandable section 6 can partially radially expand, as shown by arrows. The radial expansion 38 of the expandable section 6 can be directionally unequal, for example, conforming to the cortical bone 92b of the vertebra 88.

During the application of the longitudinal force, the unexpandable section 4 of the expandable attachment device 2 can remain substantially stationary, for example, due to normal resistive forces from the surrounding tissue in vivo, and/or due to external resistive forces 84 deployed by the deployment tool 16, for example on the distal end 8 of the expandable attachment device 2 (e.g., as shown in FIG. 31c), FIGS. 44 and 45 illustrate additional application of longitudinal force, as shown by arrow 36, by the deployment tool 16. The expandable section 6 can more fully radially expand, as shown by arrows 38, compared to the partial radial expansion shown in FIG. 43. The expandable section 6 can further radially expand to conform to the inner surface of the cortical bone 92b.

Figure 46:
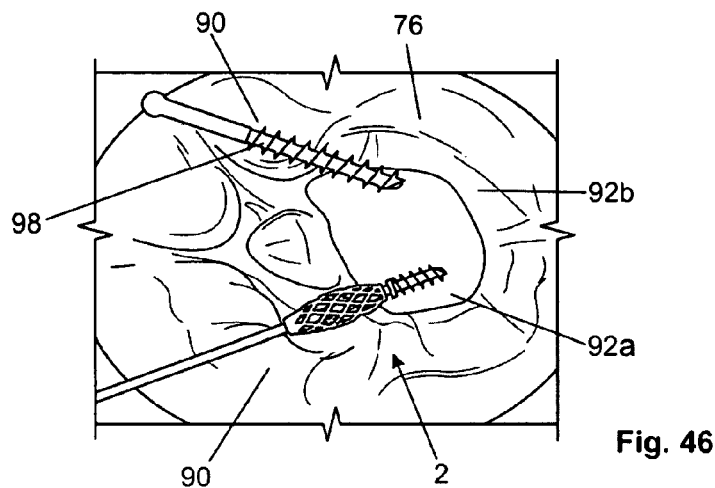
FIG. 46 is a visualization image of a non-expandable screw and an expanded expandable attachment device in a vertebral body.

FIG. 46 illustrates that a non-expandable screw 98 and an expandable attachment device 2 can be inserted into the same vertebral body 76.

Figure 47:
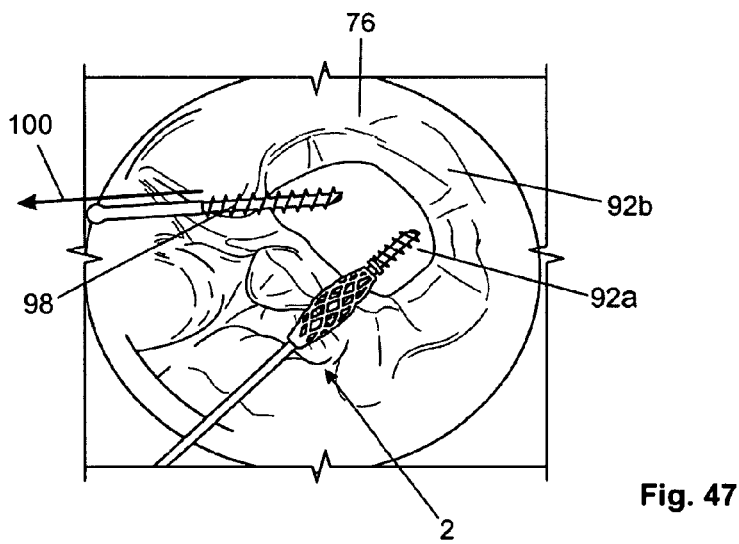
FIGS. 47 and 48 are visualization images of a withdrawal tests for a non-expandable screw and an expanded expandable attachment device, respectively, in a vertebral body.

FIG. 47 illustrates that the non-expandable screw 98 can be forcibly withdrawn, as shown by arrow 100, from the vertebral body 76 by a screw translational withdrawal force. The minimum screw translational withdrawal force needed to remove the non-expandable screw 98 from the vertebral body 76 without rotating the non-expandable screw 98 can be, for example, about 400 N (90 lbs.).

Figure 48:
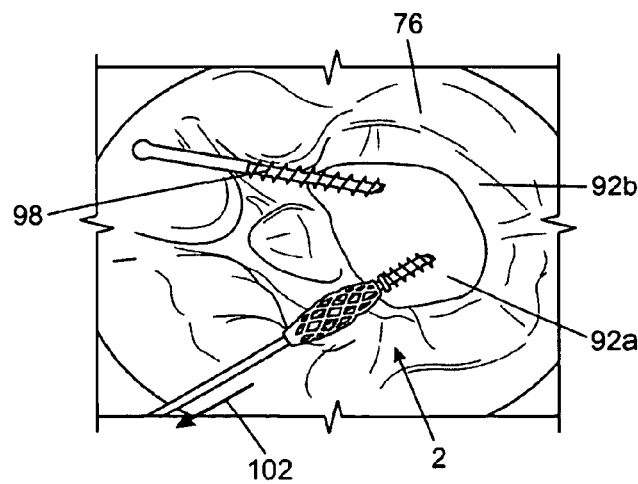

FIG. 48 illustrates that the expandable attachment device 2 can be forcibly withdrawn, as shown by arrow 102, from the vertebral body 76 by an expandable attachment device translational withdrawal force 102. The minimum expandable attachment device translational withdrawal force 102 needed to remove the expandable attachment device 2 from the vertebral body 76 without rotating or radially contracting the non-expandable screw 98 can be, for example, about 556 N (125 lbs.).

Figure 49:
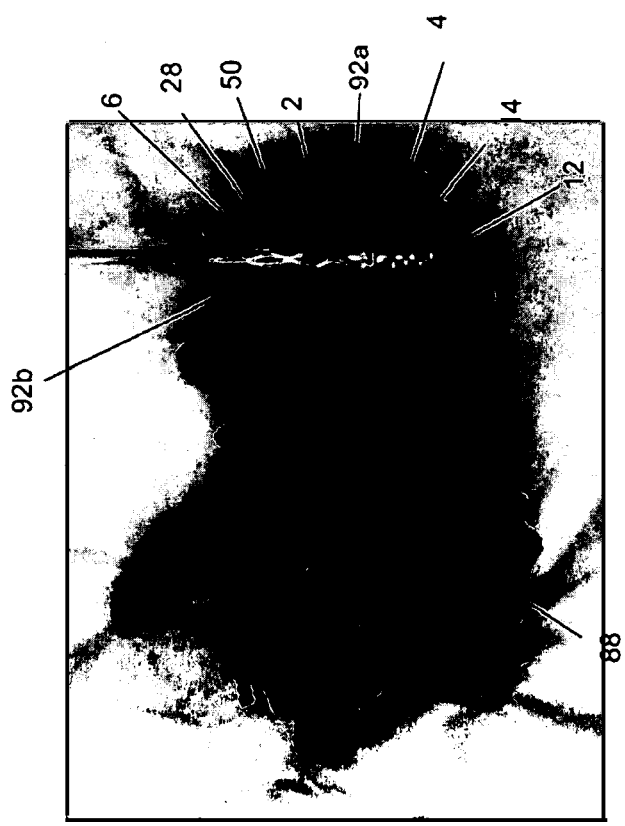
FIG. 49 illustrates a section from a bone with a deployed expandable attachment device after a withdrawal test.

FIG. 49 illustrates that the after use (e.g., a high expandable attachment device translational withdrawal force applied) the cortical bone 92b surrounding the deployed expandable attachment device 2 can be substantially unaffected. The struts 26 can distribute withdrawal forces across a large area of cancellous and cortical bone 92a and 92b, for example reducing pressure compared with a comparable non-expandable screw 98.

FIG. 50 illustrates that a second expandable attachment device 2b can be deployed inside of a first expandable attachment device 2a. For example, the second unexpandable section 22 and, optionally, the second expandable section 22 can be longitudinally placed inside the expanded or unexpanded first expandable section 20. The first expandable section 20 can be expanded before of after the introduction of the second expandable attachment device 2b in the first expandable section 20. For example, the first expandable section 20 can be radially expanded by the expansion of the second expandable section 22.

The cells on the first expandable attachment device 2a can be obstructed (i.e., be out of phase or out of sequence) by the struts 26 of the second expandable attachment device 2b, and/or the cells 50 on the first expandable attachment device 2b can be open and align (i.e., be in phase or in sequence) with the cells 50 of the second expandable attachment device 2b. Filler can be introduced into the second expandable attachment device 2b and deployed through the cells 50 of the first and second expandable attachment devices 2b into the target site.

Any or all elements of the expandable attachment device 2 and/or other devices or apparatuses described herein can be made from, for example, a single or multiple stainless steel alloys, nickel titanium alloys (e.g., Nitinol), cobalt-chrome alloys (e.g., ELGILOY® from Elgin Specialty Metals, Elgin, Ill.; CONICHROME® from Carpenter Metals Corp., Wyomissing, Pa.), nickel-cobalt alloys (e.g., MP35N® from Magellan Industrial Trading Company, Inc., Westport, Conn.), molybdenum alloys (e.g., molybdenum TZM alloy, for example as disclosed in International Pub. No. WO 03/082363 A2, published 9 Oct. 2003, which is herein incorporated by reference in its entirety), tungsten-rhenium alloys, for example, as disclosed in International Pub. No. WO 03/082363, polymers such as polyethylene teraphathalate (PET), polyester (e.g., DACRON® from E. I. Du Pont de Nemours and Company, Wilmington, Del.), poly ester amide (PEA), polypropylene, aromatic polyesters, such as liquid crystal polymers (e.g., Vectran, from Kuraray Co., Ltd., Tokyo, Japan), ultra high molecular weight polyethylene (i.e., extended chain, high-modulus or high-performance polyethylene) fiber and/or yarn (e.g., SPECTRA® Fiber and SPECTRA® Guard, from Honeywell International, Inc., Morris Township, N.J., or DYNEEMA® from Royal DSM N.V., Heerlen, the Netherlands), polytetrafluoroethylene (PTFE), expanded PTFE (ePTFE), polyether ketone (PEK), polyether ether ketone (PEEK), poly ether ketone ketone (PEKK) (also poly aryl ether ketone ketone), nylon, polyether-block co-polyamide polymers (e.g., PEBAX® from ATOFINA, Paris, France), aliphatic polyether polyurethanes (e.g., TECOFLEX® from Thermedics Polymer Products, Wilmington, Mass.), polyvinyl chloride (PVC), polyurethane, thermoplastic, fluorinated ethylene propylene (FEP), absorbable or resorbable polymers such as polyglycolic acid (PGA), poly-L-glycolic acid (PLGA), polylactic acid (PLA), poly-L-lactic acid (PLLA), polycaprolactone (PCL), polyethyl acrylate (PEA), polydioxanone (PDS), and pseudo-polyamino tyrosine-based acids, extruded collagen, silicone, zinc, echogenic, radioactive, radiopaque materials, a biomaterial (e.g., cadaver tissue, collagen, allograft, autograft, xenograft, bone cement, morselized bone, osteogenic powder, beads of bone) any of the other materials listed herein or combinations thereof. Examples of radiopaque materials are barium sulfate, zinc oxide, titanium, stainless steel, nickel-titanium alloys, tantalum and gold.

Any or all elements of the expandable attachment device 2 and/or other devices or apparatuses described herein, can be, have, and/or be completely or partially coated with agents for cell ingrowth.

The expandable attachment device 2 and/or elements of the expandable attachment device 2 and/or other devices or apparatuses described herein can be filled, coated, layered and/or otherwise made with and/or from cements, fillers, and/or glues known to one having ordinary skill in the art and/or a therapeutic and/or diagnostic agent. Any of these cements and/or fillers and/or glues can be osteogenic and osteoinductive growth factors.

Examples of such cements and/or fillers includes bone chips, demineralized bone matrix (DBM), calcium sulfate, coralline hydroxyapatite, biocoral, tricalcium phosphate, calcium phosphate, polymethyl methacrylate (PMMA), biodegradable ceramics, bioactive glasses, hyaluronic acid, lactoferrin, bone morphogenic proteins (BMPs) such as recombinant human bone morphogenetic proteins (rhBMPs), other materials described herein, or combinations thereof.

The agents within these matrices can include any agent disclosed herein or combinations thereof, including radioactive materials; radiopaque materials; cytogenic agents; cytotoxic agents; cytostatic agents; thrombogenic agents, for example polyurethane, cellulose acetate polymer mixed with bismuth trioxide, and ethylene vinyl alcohol; lubricious, hydrophilic materials; phosphor cholene; anti-inflammatory agents, for example non-steroidal anti-inflammatories (NSAIDs) such as cyclooxygenase-1 (COX-1) inhibitors (e.g., acetylsalicylic acid, for example ASPIRIN® from Bayer AG, Leverkusen, Germany; ibuprofen, for example ADVIL® from Wyeth, Collegeville, Pa.; indomethacin; mefenamic acid), COX-2 inhibitors (e.g., VIOXX® from Merck & Co., Inc., Whitehouse Station, N.J.; CELEBREX® from Pharmacia Corp., Peapack, N.J.; COX-1 inhibitors); immunosuppressive agents, for example Sirolimus (RAPAMUNE®, from Wyeth, Collegeville, Pa.), or matrix metalloproteinase (MMP) inhibitors (e.g., tetracycline and tetracycline derivatives) that act early within the pathways of an inflammatory response. Examples of other agents are provided in Walton et al, Inhibition of Prostoglandin $E_2$ Synthesis in Abdominal Aortic Aneurysms, *Circulation*, Jul. 6, 1999, 48-54; Tambiah et al, Provocation of Experimental Aortic Inflammation Mediators and Chlamydia Pneumoniae, *Brit. J Surgery* 88 (7), 935-940; Franklin et al, Uptake of Tetracycline by Aortic Aneurysm Wall and Its Effect on Inflammation and Proteolysis, *Brit. J Surgery* 86 (6), 771-775; Xu et al, Spl Increases Expression of Cyclooxygenase-2 in Hypoxic Vascular Endothelium, *J. Biological Chemistry* 275 (32) 24583-24589; and Pyo et al, Targeted Gene Disruption of Matrix Metalloproteinase-9 (Gelatinase B) Suppresses Development of Experimental Abdominal Aortic Aneurysms, *J. Clinical Investigation* 105 (11), 1641-1649 which are all incorporated by reference in their entireties.

Other examples of fractures types that can be treated with the disclosed device and method include Greenstick fractures, transverse fractures, fractures across growth plates, simple fractures, wedge fractures, complex fractures, compound fractures, complete fractures, incomplete fractures, linear fractures, spiral fractures, transverse fractures, oblique fractures, comminuted fractures, impacted fractures, and soft tissue tears, separations (e.g., avulsion fracture), sprains, and combinations thereof. Plastic deformations of bones can also be treated with the disclosed device and method.

Other examples of bones that can be treated with the disclosed device and method include the fingers (e.g., phalanges), hands (e.g., metacarpals, carpus), toes (e.g., tarsals), feet (metatarsals, tarsus), legs (e.g., femur, tibia, fibula), arms (e.g., humerus, radius, ulna), scapula, coccyx, pelvis, clavicle, scapula, patella, sternum, ribs, or combinations thereof.

Devices, elements and configurations disclosed as expandable support devices in the following applications can be used for the expandable section 6 in the present application, and the following applications are incorporated by reference herein in their entireties: PCT Application No. 2005/034115 filed Sep. 21, 2005, PCT Application No. 2006/016553 filed Apr. 27, 2006, PCT Application No. 2005/034742 filed Sep. 26, 2005, PCT Application No. 2005/034728 filed Sep. 26, 2005, PCT Application No. 2005/037126 filed Oct. 12, 2005, PCT Application No. 2006/062333 filed Dec. 19, 2006, PCT Application No. 2006/038920 filed Oct. 4, 2006, PCT Application No. 2006/027601 filed Jul. 14, 2006, PCT Application No. 2006/062201 filed Dec. 15, 2006, PCT Application No. 2006/062339 filed Dec. 19, 2006, PCT Application No. 2006/048667 filed Dec. 19, 2006, and U.S. patent application Ser. No. 11/457,772 filed Jul. 14, 2006.

All dimensions shown herein are exemplary. The dimensions shown herein can at least be expanded to ranges from about 50% to about 150% of the exemplary dimension shown herein, more narrowly from about 75% to about 125% of the exemplary dimension shown herein.

The use of the term "radial expansion" herein refers to both a volumetric increase of an element, or an increase in the radial dimension of the element itself, or the increase in the maximum radius of the element as measured from the expandable attachment device axis 10.

Any elements described herein as singular can be pluralized (i.e., anything described as "one" can be more than one). Any species element of a genus element can have the characteristics or elements of any other species element of that genus. The above-described configurations, elements or complete assemblies and methods and their elements for carrying out the invention, and variations of aspects of the invention can be combined and modified with each other in any combination.

We claim:

1. An attachment device for biological implantation having a longitudinal axis and a longitudinal length, a distal end and a proximal end having a tip, wherein the longitudinal axis and spans from the tip to the distal end, comprising:
   a screw having a radially expandable section and a radially non-expandable section, wherein the radially expandable section has an expandable section distal end and a radially expandable radius, and wherein the screw has a first cell and a second cell, and wherein the first cell is longitudinally offset from the second cell; and
   an expander element slidably received by the screw, wherein the expander element comprises an expander head, and a first expander shaft longitudinally extending from the expander head; and
   wherein the screw comprises radially extending threads, and wherein the expander element comprises radially extending threads; and
   wherein the screw has a first configuration, and wherein the screw has a second configuration where the expander element is slid along the screw, and wherein the radius of the expandable section distal end in the first configuration is equal to the radius of the expandable section distal end in the second configuration.

2. The device of claim 1, wherein the radially expandable radius is configured to radially expand when the longitudinal length is longitudinally contracted.

3. The device of claim 1, further comprising a fixation joint rotatably attached to the screw, wherein the fixation joint is configured to attach to a separate device.

4. The device of claim 3, wherein the fixation joint is rotatably attached to the screw with more than one degree of rotational freedom.

5. The device of claim 1, wherein the radially expandable section comprises two struts.

6. The device of claim 1, wherein the attachment device has an attachment device longitudinal axis, and wherein at least a portion of the longitudinal axis comprises a substantially curved configuration.

7. The device of claim 1, wherein the expander element is substantially planar.

8. The device of claim 1, wherein the first cell is in the radially expandable section of the screw.

9. The device of claim 8, wherein the first cell is oriented longitudinally along the longitudinal axis of the attachment device.

10. The device of claim 9, wherein he first cell comprises an A-shaped cell.

11. The device of claim 9, wherein the first cell comprises a V-shaped cell.

12. The device of claim 9, wherein the first cell comprises a W-shaped cell.

13. The device of claim 9, wherein the first cell comprises a helical cell.

14. The device of claim 9, wherein the first cell comprises a diamond-shaped cell.

15. The device of claim 1, further comprising a filler inside of the screw.

16. The device of claim 1, further comprising a distal end cap at a distal end of the screw or the expander element, wherein the distal end cap comprises an interface configured to attach to a deployment tool.

17. The device of claim 16, wherein the distal end cap is substantially spherical.

18. The device of claim 1, further comprising a fixation joint attached to a distal end of the screw or the expander element.

19. The device of claim 18, wherein the fixation joint is polyaxially rotatable with respect to the screw and/or the expander element.

20. An attachment device for biological implantation having a longitudinal axis and a longitudinal length, a distal end and a proximal end having a tip, wherein the longitudinal axis spans from the tip to the distal end, comprising:
- a screw having a radially expandable section and a radially non-expandable section, wherein the radially expandable section has an expandable section distal end and a radially expandable radius, and wherein the screw has a first cell and a second cell, and wherein the first cell is longitudinally offset from the second cell;
- wherein the screw comprises radially extending threads, and wherein the first cell longitudinally overlaps with at least some of the radially extending threads; and
- wherein the screw has a first configuration, and wherein the screw has a second configuration where an expander element is slid along the screw, and wherein the radius of the expandable section distal end in the first configuration is equal to the radius of the expandable section distal end in the second configuration.

21. An attachment device for biological implantation having a longitudinal axis and a longitudinal length, a distal end and a proximal end having a tip, wherein the longitudinal axis spans from the tip to the distal end, comprising:
- a screw having a radially expandable section and a radially non-expandable section, wherein the radially expandable section has an expandable section distal end and a radially expandable radius, and wherein the screw has a first cell and a second cell, and wherein the first cell is longitudinally offset from the second cell; and
- wherein the screw comprises radially extending threads; and
- wherein the screw has a first configuration, and wherein the screw has a second configuration where an expander element is slid along the screw, and wherein the radius of the expandable section distal end in the first configuration is equal to the radius of the expandable section distal end in the second configuration.

22. The device of claim 21, further comprising a fixation joint polyaxially rotatably attached to a distal end of the screw.

* * * * *

UNITED STATES PATENT AND TRADEMARK OFFICE
CERTIFICATE OF CORRECTION

| | | |
|---|---|---|
| PATENT NO. | : 8,636,784 B2 | Page 1 of 1 |
| APPLICATION NO. | : 12/264181 | |
| DATED | : January 28, 2014 | |
| INVENTOR(S) | : E. Skott Greenhalgh et al. | |

It is certified that error appears in the above-identified patent and that said Letters Patent is hereby corrected as shown below:

In the Claims:

Col. 12, in claim 1, line 28, please replace "longitudinal axis and spans" with -- longitudinal axis spans --.

Col. 13, in claim 10, line 4, please replace "he" with -- the --.

Signed and Sealed this
Twenty-seventh Day of May, 2014

Michelle K. Lee
*Deputy Director of the United States Patent and Trademark Office*